US009701704B2

(12) United States Patent
Lee et al.

(10) Patent No.: US 9,701,704 B2
(45) Date of Patent: Jul. 11, 2017

(54) CATALYSTS FOR (E)-SELECTIVE OLEFIN METATHESIS

(71) Applicant: CALIFORNIA INSTITUTE OF TECHNOLOGY, Pasadena, CA (US)

(72) Inventors: Choon Woo Lee, La Canada, CA (US); Robert H. Grubbs, South Pasadena, CA (US); Pablo E. Guzman, Proving Ground, MD (US); Tonia S. Ahmed, Pasadena, CA (US); T. Patrick Montgomery, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/074,545

(22) Filed: Mar. 18, 2016

(65) Prior Publication Data
US 2017/0022231 A1    Jan. 26, 2017

Related U.S. Application Data

(60) Provisional application No. 62/135,797, filed on Mar. 20, 2015, provisional application No. 62/180,183, filed on Jun. 16, 2015.

(51) Int. Cl.
| | | |
|---|---|---|
| *C07F 15/00* | (2006.01) | |
| *B01J 31/28* | (2006.01) | |
| *C07C 67/30* | (2006.01) | |
| *C07D 313/00* | (2006.01) | |
(Continued)

(52) U.S. Cl.
CPC ......... *C07F 15/0046* (2013.01); *B01J 31/122* (2013.01); *C07C 67/30* (2013.01); *C07C 67/475* (2013.01); *C07D 313/00* (2013.01); *B01J 31/28* (2013.01); *B01J 2231/543* (2013.01); *B01J 2531/821* (2013.01); *C07B 2200/09* (2013.01);
(Continued)

(58) Field of Classification Search
CPC .... C07F 15/0046; C07F 15/02; C07F 15/002; B01J 2531/821; B01J 2531/842; B01J 2531/825
See application file for complete search history.

(56) References Cited

U.S. PATENT DOCUMENTS

| | | |
|---|---|---|
| 5,312,940 A | 5/1994 | Grubbs et al. |
| 6,620,955 B1 | 9/2003 | Pederson et al. |
| 6,921,735 B2 | 7/2005 | Hoveyda et al. |
(Continued)

FOREIGN PATENT DOCUMENTS

WO          02/14376 A2    2/2002

OTHER PUBLICATIONS

Manzini, S.; Urbina Blanco, C.A.; Slawin, A.M.Z.; Nolan, S.P. Organometallics, 2012, 31, 6514-6517.*
(Continued)

*Primary Examiner* — Rip A Lee
(74) *Attorney, Agent, or Firm* — J.A. Lindeman & Co., PLLC

(57) ABSTRACT

This invention relates generally to olefin metathesis catalyst compounds, to the preparation of such compounds, and the use of such catalysts in the metathesis of olefins and olefin compounds, more particularly, in the use of such catalysts in (E)-selective olefin metathesis reactions. The invention has utility in the fields of catalysis, organic synthesis, polymer chemistry, and industrial and fine chemicals chemistry.

22 Claims, 14 Drawing Sheets

(51) Int. Cl.
  *C07C 67/475* (2006.01)
  *B01J 31/12* (2006.01)
(52) U.S. Cl.
  CPC ...... *C07C 2101/08* (2013.01); *C08F 2500/25* (2013.01)

(56) References Cited

U.S. PATENT DOCUMENTS

| | | | |
|---|---|---|---|
| 7,026,495 B1 | 4/2006 | Pederson et al. | |
| 2003/0100776 A1* | 5/2003 | Grubbs | C07C 6/04 549/513 |
| 2014/0371454 A1* | 12/2014 | Hoveyda | B01J 31/2278 546/4 |

OTHER PUBLICATIONS

Endo & Grubbs, "Chelated Ruthenium Catalysis for Z-Selective Olefin Metathesis," J. Am. Chem. Soc., 2011, 133, pp. 8525-8527.
Furstner et al., "Total Synthesis of (−)-Salicylihalamide," Chem. Eur. J. 2001, 7, No. 24, pp. 5286-5298.
Furstner & Radkowski, "A chemo- and stereselective reduction of cycloalkynes to (E)-cycloallkenes," Chem. Commun., 2002, pp. 2182-2183.
Furstner, "Teaching Metathesis "Simple" Stereochemistry," Science, vol. 341, 2013, pp. 1229713-1-1229713-7.
Greene et al., "Protective Groups in Organic Synthesis," Third Edition, John Wiley & Sons, Inc.
Keitz et al., "Z-Selective Homodimerization of Terminal Olefins with a Ruthenium Metathesis Catalyst," J. Am. Chem. Soc., 2011, 133, pp. 9686-9688.
Keitz et al., "Improved Ruthenium Catalysts for Z-Selective Olefin Metathesis," J. Am. Chem. Soc., 2012, 134, pp. 693-699.
Lehr et al., "Total Synthesis of Tulearin C**," Angew. Chem. Int. Ed. 2011, 50, pp. 11373-11377.
Liu et al., "Z-Selective in Olefin Metathesis with Chelated Ru Catalysts: Computational Studies of Mechanism and Selectivity," J. Am. Chem. Soc., 2012, 134, pp. 1464-1467.
Luan et al., "Identification and Characterization of a New Family of Catalytically Highly Active Imidazolin-2-ylidenes," J. Am. Chem. Soc., 2008, 130, pp. 6848-6858.
Matsui et al., "Unusual E-Selective Ring-Closing Metathesis to Form Eight-Membered Rings **," Angew. Chem. Int. Ed. 2010, 49, pp. 10068-10073.
Rost et al., "A hexafluorobenzene promoted ring-closing metathesis to form tetrasubstituted olefins," Tetrahedron Lett. 49, (2008), pp. 5968-5971.

\* cited by examiner

ID
CATALYSTS FOR (E)-SELECTIVE OLEFIN METATHESIS

RELATED APPLICATIONS

This application claims the benefit of U.S. Provisional Patent Application No. 62/135,797, filed Mar. 20, 2015, and of U.S. Provisional Patent Application No. 62/180,183, filed Jun. 16, 2015, the contents of each are incorporated herein by reference.

STATEMENT OF FEDERAL SUPPORT

This invention was made with government support under GM031332 awarded by the National Institutes of Health and CHE1212767 awarded by the National Science Foundation. The government has certain rights in the invention.

TECHNICAL FIELD

This invention relates generally to olefin metathesis catalyst compounds, to the preparation of such compounds, and the use of such catalysts in the metathesis of olefins and olefin compounds, more particularly, in the use of such catalysts in (E)-selective olefin metathesis reactions. The invention has utility in the fields of catalysis, organic synthesis, polymer chemistry, and industrial and fine chemicals chemistry.

BACKGROUND

Since its discovery in the 1950s, olefin metathesis has emerged as a valuable synthetic method for the formation of carbon-carbon double bonds. In particular, its recent advances in applications to organic syntheses and polymer syntheses mostly rely on developments of well-defined catalysts. Among attempts to improve catalyst efficiency over the past decade, one of the most attractive frontiers has been selective synthesis of stereo-controlled olefin products. Most catalysts give higher proportion of thermodynamically favored (E) isomer of olefin products.

SUMMARY OF THE DISCLOSURE

The invention is directed to addressing one or more of the aforementioned concerns, and, in one embodiment, provides metal carbene olefin metathesis catalysts that may be used in the invention disclosed herein. The metal carbene olefin metathesis catalysts are preferably Group 8 transition metal complexes. The invention is also directed to a method of preparing the metal carbene olefin metathesis catalysts, of the invention.

In one embodiment the present invention provides metal carbene olefin metathesis catalysts for (E)-selective olefin metathesis.

In another embodiment the present invention provides metal carbene olefin metathesis catalysts for (E)-selective ring opening metathesis polymerization (ROMP).

In another embodiment the present invention provides metal carbene olefin metathesis catalysts for (E)-selective ring opening cross metathesis (ROCM).

In another embodiment the present invention provides metal carbene olefin metathesis catalysts for (E)-selective cross metathesis (CM).

In another embodiment the present invention provides metal carbene olefin metathesis catalysts for (E)-selective ring closing metathesis (RCM).

In another embodiment the present invention provides a method for performing a metathesis reaction comprising, contacting at least one olefin with a metal carbene olefin metathesis catalyst of the invention.

DETAILED DESCRIPTION OF THE DISCLOSURE

Terminology and Definitions

Figure 1:
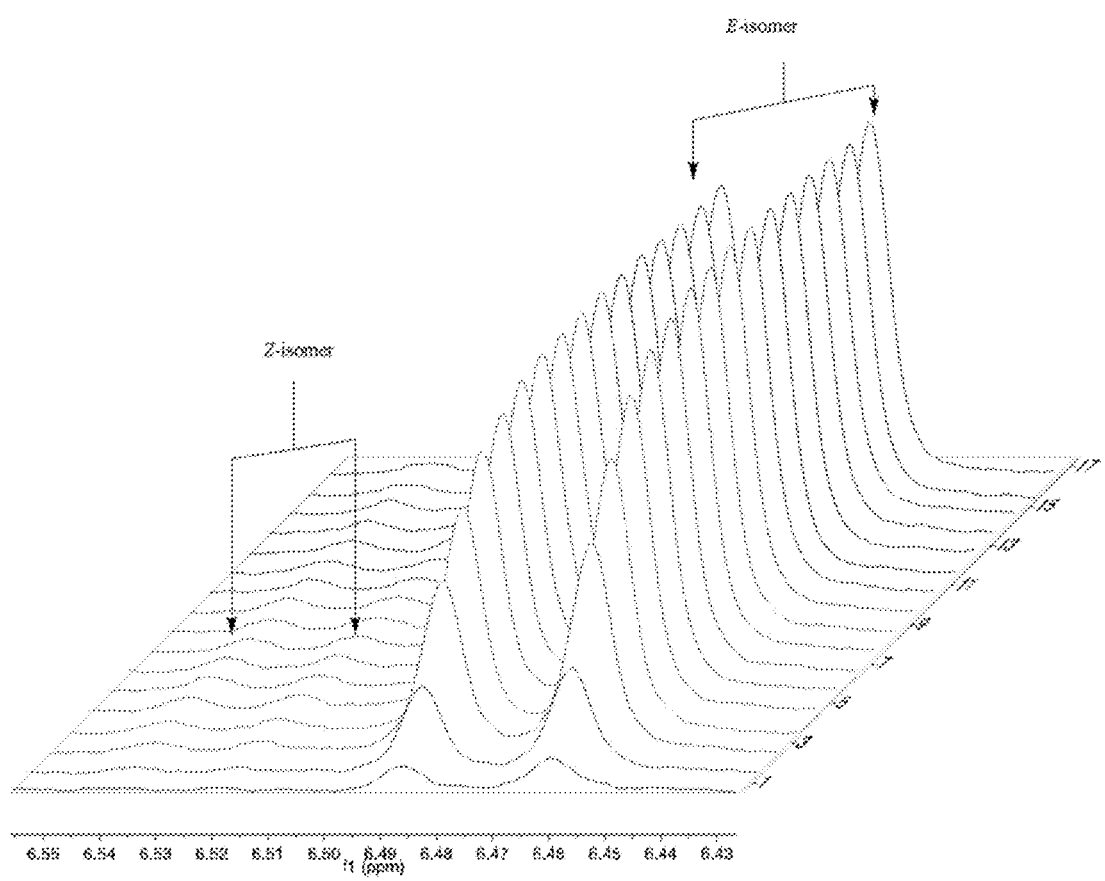
FIG. 1 shows the $^1$H-NMR array experiment in the ROCM reaction of 2,3-dihydrofuran with catalyst (3)-rac, as shown in Table 1 entry 3.

Unless otherwise indicated, the invention is not limited to specific reactants, substituents, catalysts, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively. The term "alkenyl" is used interchangeably with the term "olefin" herein.

The geometry of the olefins described in this patent application may be of (E) conformation, or of (Z) conformation, or of a mixture of (E) and (Z) conformations. Applicants have represented a mixture of double-bond isomers by using a squiggly bond

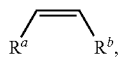

For example, as represented herein, structure

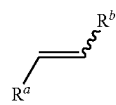

exemplifies either the (E) conformation

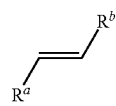

or the (Z) conformation $$R^a \diagup\!\!=\!\!\diagdown R^b,$$

or can represent a mixture of (E) and (Z) conformations.

The term "(E/Z) ratio" refers to proportion of (E) isomer versus (Z) isomer.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl," and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo," "halogen," and "halide" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_1$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^{31}$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR═NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO₂—OH), sulfonato (—SO₂—O⁻), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO₂-alkyl), $C_1$-$C_{24}$ monoalkylaminosulfonyl-SO₂—N(H) alkyl), $C_1$-$C_{24}$ dialkylaminosulfonyl —SO₂—N(alkyl)₂, $C_5$-$C_{24}$ arylsulfonyl (—SO₂-aryl), boryl (—BH₂), borono (—B(OH)₂), boronato (—B(OR)₂ where R is alkyl or other hydrocarbyl), phosphono (—P(O)(OH)₂), phosphonato (—P(O)(O⁻)₂), phosphinato (—P(O)(O⁻)), phospho (—PO₂), and phosphino (—PH₂); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Controlling the Formation of the (E)-Isomer in Metathesis Reactions

Olefin metathesis is a powerful method for the synthesis of C=C bonds in a variety of synthetic contexts, including organic synthesis, polymer chemistry, materials science, and biochemistry. Control of olefin geometry is frequently crucial to controlling the properties of a molecule, leading synthetic chemists to develop numerous stereoselective olefination methods. While recent advances have uncovered a family of (Z)-selective olefin metathesis catalysts, complexes capable of kinetically controlled (E)-selective cross metathesis remain elusive (Furstner, A., Teaching Metathesis "Simple" Stereochemistry. Science 2013, 341, 1357). As a consequence, chemists have relied on the rapid rates of equilibration during olefin metathesis and the thermodynamic stability of (E) olefins to generate (E) products. Scheme 1a and Scheme 1b show the (E/Z) selectivity in olefin metathesis by second generation Grubbs catalysts.

Scheme 1a

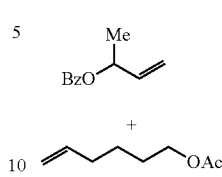
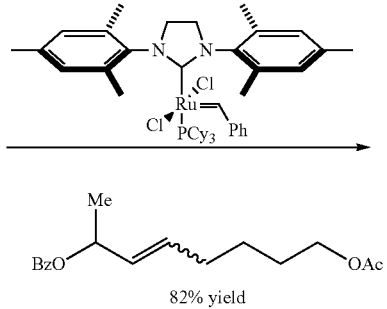

82% yield

10:1 E/Z ratio

Scheme 1b

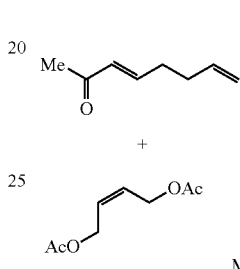
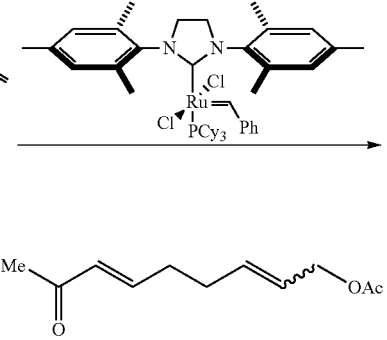

78% yield 4.5:1 E/Z ratio

However, in many contexts, the relative energies of (E) and (Z) isomers are similar, resulting in mixtures as shown in Scheme 1c (Furstner, A.; Dierkes, T.; Thiel, O. R.; Blanda, G., Total synthesis of (−)-salicylihalamide. Chem. Eur. J. 2001, 7, 5286-5298).

Scheme 1c

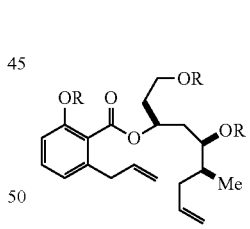
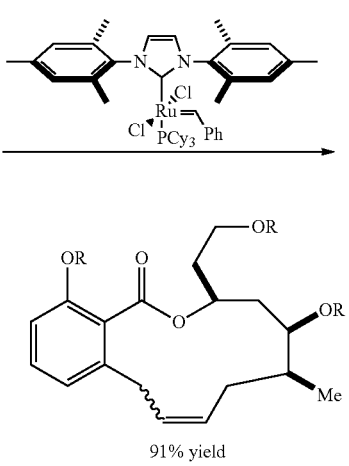

91% yield

40:60 (E/Z) ratio

Indirect solutions to this problem have required alkyne metathesis/semi-reduction, ((a) Furstner, A.; Radkowski, K., A chemo- and stereoselective reduction of cycloalkynes to (E) cycloalkenes. Chem. Commun. 2002, 2182-2183; (b)

Lehr, K.; Mariz, R.; Leseurre, L.; Gabor, B.; Fuerstner, A., Total Synthesis of Tulearin C. *Angew. Chem., Int. Ed.* 2011, 50, 11373-11377); temporary auxiliary groups, or conformational control, (Matsui, R.; Seto, K.; Fujita, K.; Suzuki, T.; Nakazaki, A.; Kobayashi, S., Unusual E-Selective Ring-Closing Metathesis To Form Eight-Membered Rings. *Angew. Chem., Int. Ed.* 2010, 49, 10068-10073), which complicate the synthetic sequence and lack generality.

In addition to the practical advantages, designing an (E)-selective metathesis catalyst presents a major intellectual challenge. The features of a (Z)-selective catalyst were straightforward but difficult to execute. For a (Z)-selective system it is apparent that one side of the metallacyclic intermediate must be sterically blocked to push all substituents to the same side of the metallacycle as shown in Scheme 2.

The development of (Z)-selective ruthenium catalysts (a) Endo, K.; Grubbs, R. H., Chelated ruthenium catalysts for (Z)-selective olefin metathesis. *J. Am. Chem. Soc.* 2011, 133, 8525-8527; (b) Keitz, B. K.; Endo, K.; Herbert, M. B.; Grubbs, R. H., (Z)-selective homodimerization of terminal olefins with a ruthenium metathesis catalyst. *J. Am. Chem. Soc.* 2011, 133, 9686-9688; (c) Keitz, B. K.; Endo, K.; Patel, P. R.; Herbert, M. B.; Grubbs, R. H., Improved ruthenium catalysts for (Z)-selective olefin metathesis. *J. Am. Chem. Soc.* 2012, 134, 693-699, required an initially unexpected cyclometalated architecture that imposed a preference for the formation of side bound metallacycles (rather than bottom-bound metallacycles normally found in non-chelated catalysts). As illustrated in Scheme 2, the side-bound intermediates place the metallacycle underneath the N substituents of the N-heterocyclic carbene (NHC) (Liu, P.; Xu, X.; Dong, X.; Keitz, B. K.; Herbert, M. B.; Grubbs, R. H.; Houk, K. N.), (Z) Selectivity in olefin metathesis with chelated Ru catalysts: computational studies of mechanism and selectivity (*J. Am. Chem. Soc.* 2012, 134, 1464-1467). We extensively investigated models for (E) selectivity using side-bound models, however, our efforts proved unfruitful, presumably due to sterically disfavor between substituent in metallacycle and bulky ligand (the right model in Scheme 2).

Scheme 3: Bottom-bound ruthenium metallacycles for (E)-selective catalysts

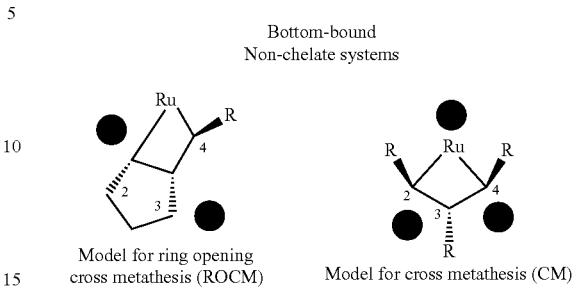

In the ROCM reaction, (substituents at C2 and C3 of metallacycle must be cis) the stereochemistry of the product is controlled by the trans stereochemistry of substituents at the C2 and C4. In the cross metathesis reactions, the stereochemistry is controlled by the trans relationship of substituents at the C3 and C4 positions and requires a third steric block that pushes the substituent at C3 to a position trans to the substituent at the C2 and C4 positions.

Exploratory studies have identified a promising candidate for a kinetically controlled (E)-selective metathesis catalyst. The inherently reversible nature of olefin metathesis often inhibits the direct measurement of (E/Z) geometries, i.e., secondary metathesis. Thus, the competency for (E)-selectivity was probed by reacting well-established Ru catalysts with 2,3-dihydrofuran. This reaction is irreversible under the given conditions and models the key step in ring opening cross metathesis. As illustrated in Table 1, the new ruthenium catalyst (3)-rac yields its corresponding Fischer carbene complex with an (E/Z) ratio of >20:1, which is significantly higher than ratio given by $1^{st}$ and $2^{nd}$ generation Grubbs catalysts, C823 (1) and C848 (2). Since under ambient reaction conditions, Fischer carbenes do not undergo further metathesis reactions, this reaction measures Scheme 2: (Z) Selective ruthenium metathesis catalyst (left) and its metallacycle intermediates to form (Z) and (E) olefins (center and right)

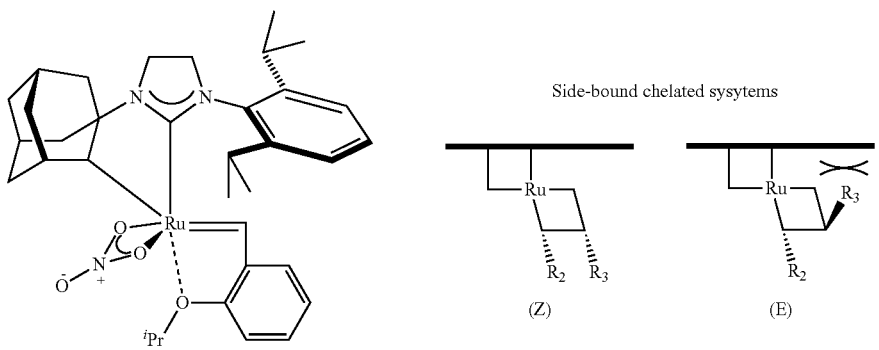

Therefore, we will explore this chemistry utilizing bottom-bound approaches. For an (E)-selective catalyst, the steric requirement is much more difficult (although the preference for (E) is already present). Also, two different designs maybe required for the standard ring opening cross metathesis (ROCM) and simple cross metathesis (CM) as shown in Scheme 3.

the inherent (E/Z) selectivity of a given catalyst. The mono ortho substituents on (3)-rac appear to provide the steric block for the C2 and C4 positions as described in Scheme 3. Furthermore, zero substitution on an ortho position can also allow the substituent at the C4 to be trans to the C2 position. FIG. 1 shows the $^1$H-NMR array experiment in the ROCM of 2,3-dihydrofuran with catalyst (3)-rac.

TABLE 1
(E/Z) Ratio metathesis of 2,3-dihydrofuran for ruthenium catalysts
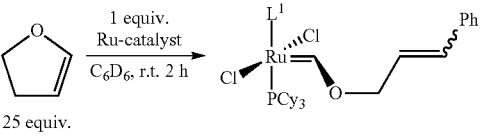
| Ru-catalyst | | L¹ | E/Z ratio |
|---|---|---|---|
| 1 | C823 | | 4:1 |
| 2 | C848 | | 6:1 |
| 3 | (3)-rac | | >20:1 |
| 4 | C849 | | ~8:1 |
| 5 | C933 | | 3:1 |
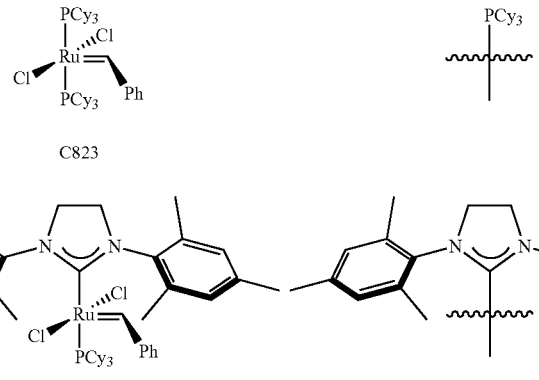
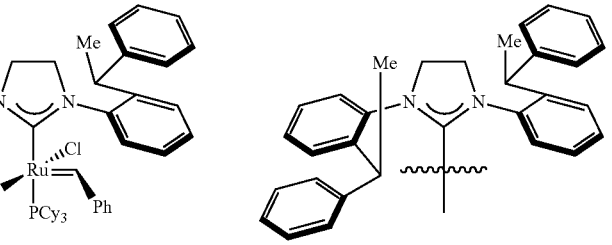
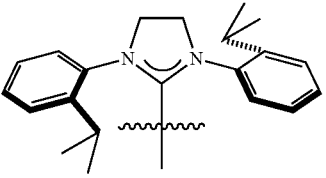
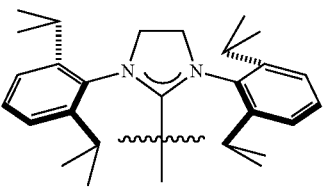

TABLE 1-continued (E/Z) Ratio metathesis of 2,3-dihydrofuran for ruthenium catalysts

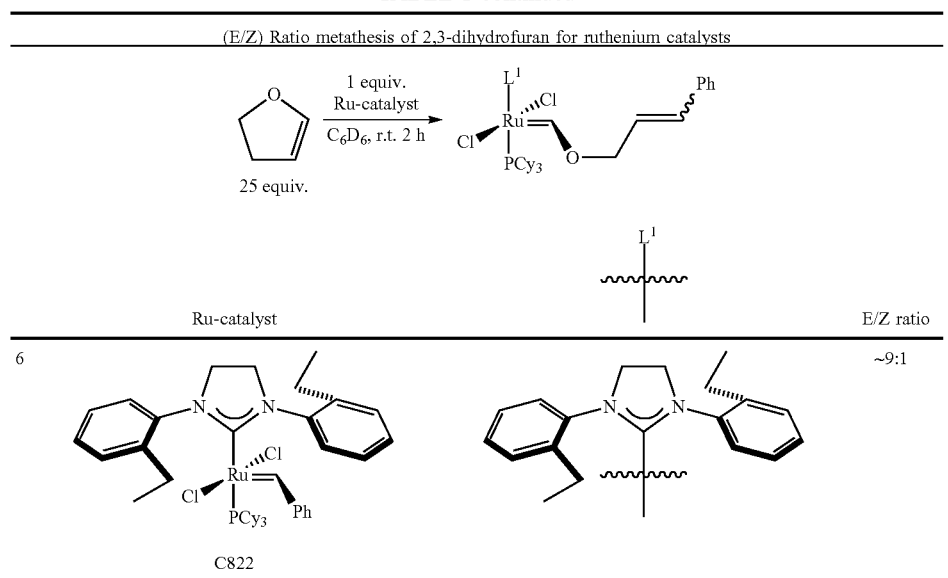

| Ru-catalyst | L¹ | E/Z ratio |
|---|---|---|
| 6 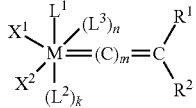 C822 | 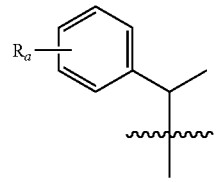 | ~9:1 |

Metal Carbene Olefin Metathesis Catalysts

A metal carbene olefin metathesis catalyst that may be used in the invention disclosed herein, is preferably a Group 8 transition metal complex having the structure of Formula (I):

Formula (I)

$$X^1\underset{X^2}{\overset{L^1}{\underset{(L^2)_k}{\vphantom{|}}}}\!\!\!\!\!\overset{(L^3)_n}{M}\!\!=\!(C)_m\!=\!C\!\!\overset{R^1}{\underset{R^2}{\vphantom{|}}}$$

in which:

M is a Group 8 transition metal;

L¹ is an N-heterocyclic carbene ligand (i.e., NHC ligand) having the structure of Formula (II) or of Formula (III):

Formula (II)

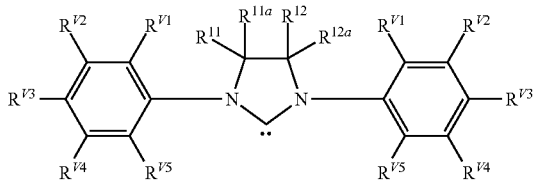

Formula (III)

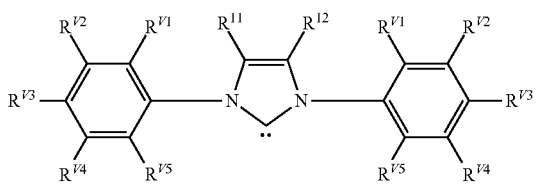

$R^{V1}$, $R^{V2}$, $R^{V3}$, $R^{V4}$, and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, substituted $C_5$-$C_{14}$ aryl;

$R^{11}$, $R^{12}$, $R^{11a}$, $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_1$-$C_{14}$ aryl, or halide; and at least one of $R^{V1}$, $R^{V2}$, $R^{V3}$, $R^{V4}$, or $R^{V5}$ is represented by a group such as:

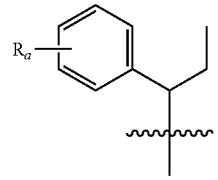

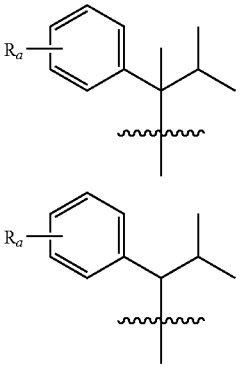

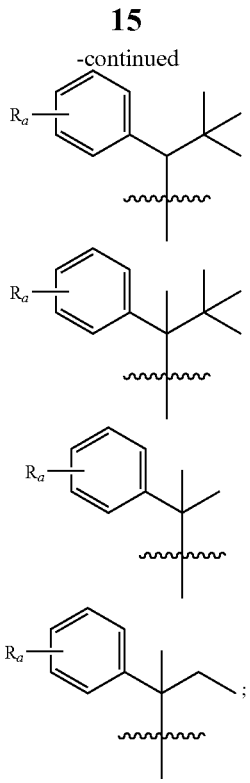

"a" represents 0, 1, 2, 3, 4, or 5;

R is substituted $C_1$-$C_6$ alkyl, $C_1$-$C_6$ alkyl, substituted $C_3$-$C_{10}$ cycloalkyl, $C_3$-$C_{10}$ cycloalkyl, or halogen;

$L^2$ and $L^3$ are neutral electron donor ligands;

n is 0 or 1, such that $L^3$ may or may not be present;

m is 0, 1, or 2;

k is 0 or 1;

$X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

Additionally, in Formula (I) one or both of $R^1$ and $R^2$ may have the structure —$(W)_n$—$U^+V^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1. Furthermore, $R^1$ and $R^2$ may be taken together to form an indenylidene moiety, preferably a phenylindenylidene moiety.

Preferred catalysts contain Ru or Os as the Group 8 transition metal, with Ru particularly preferred.

Numerous embodiments of the catalysts useful in the reactions disclosed herein are described in more detail infra. For the sake of convenience, the catalysts are described in groups, but it should be emphasized that these groups are not meant to be limiting in any way. That is, any of the catalysts useful in the invention may fit the description of more than one of the groups described herein.

For the first group of catalysts, n is 0, and $L^2$ is selected from phosphine, sulfonated phosphine, phosphite, phosphinite, phosphonite, arsine, stibine, ether, (including cyclic ethers), amine, amide, imine, sulfoxide, carboxyl, nitrosyl, pyridine, substituted pyridine, imidazole, substituted imidazole, pyrazine, substituted pyrazine and thioether. Exemplary ligands are trisubstituted phosphines. Preferred trisubstituted phosphines are of the formula $PR^{H1}R^{H2}R^{H3}$, where $R^{H1}$, $R^{H2}$, and $R^{H3}$ are each independently substituted or unsubstituted aryl or $C_1$-$C_{10}$ alkyl, particularly primary alkyl, secondary alkyl, or cycloalkyl. In the most preferred embodiment, $L^2$ is selected from the group consisting of trimethylphosphine ($PMe_3$), triethylphosphine ($PEt_3$), tri-n-butylphosphine ($PBu_3$), tri(ortho-tolyl)phosphine (P-o-$tolyl_3$), tri-tert-butylphosphine (P-tert-$Bu_3$), tricyclopentylphosphine ($PCyclopentyl_3$), tricyclohexylphosphine ($PCy_3$), triisopropylphosphine (P-i-$Pr_3$), trioctylphosphine ($POct_3$), triisobutylphosphine, (P-i-$Bu_3$), triphenylphosphine ($PPh_3$), tri(pentafluorophenyl)phosphine ($P(C_6F_5)_3$), methyldiphenylphosphine ($PMePh_2$), dimethylphenylphosphine ($PMe_2Ph$), and diethylphenylphosphine ($PEt_2Ph$). Alternatively, $L^2$ may be selected from phosphabicycloalkane (e.g., monosubstituted 9-phosphabicyclo-[3.3.1]nonane, or monosubstituted 9-phosphabicyclo[4.2.1]nonane] such as cyclohexylphoban, isopropylphoban, ethylphoban, methylphoban, butylphoban, pentylphoban and the like).

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, $NO_3$, —N=C=O, —N=C=S, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, R¹ is hydrogen and R² is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, R² is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, R² is phenyl or vinyl substituted with one or more moieties selected from methyl, ethyl, chloro, bromo, iodo, fluoro, nitro, dimethylamino, methyl, methoxy, and phenyl. Optimally, R² is phenyl or —CH═C(CH₃)₂.

Any two or more (typically two, three, or four) of $X^1$, $X^2$, $L^1$, $L^2$, $L^3$, $R^1$, and $R^2$ be taken together to form a cyclic group, including bidentate or multidentate ligands, as disclosed, for example, in U.S. Pat. No. 5,312,940, the disclosure of which is incorporated herein by reference. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7, or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

The Group 8 transition metal complex having the structure of Formula (I) may be in a racemic isomeric form, a meso isomeric form, or a mixture of the racemic and meso isomeric forms.

In another embodiment, metal carbene olefin metathesis catalysts of the invention comprise a Group 8 transition metal complex having the structure of Formula (IV):

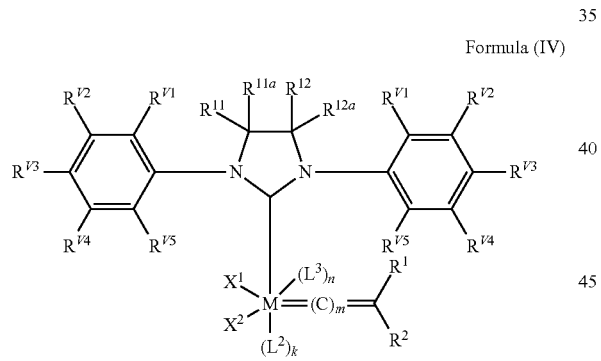

Formula (IV)

wherein:

M is Ru or Os;

$R^{V1}$, $R^{V2}$, $R^{V3}$, $R^{V4}$, and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, substituted $C_5$-$C_{14}$ aryl;

$R^{11}$, $R^{12}$, $R^{11a}$, and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide;

$X^1$ and $X^2$ are independently halogen;

$L^2$ and $L^3$ are neutral electron donor ligands, wherein $L^2$ and/or $L^3$ may be linked with $R^1$ or $R^2$ to form one or more cyclic groups;

n is 0 or 1, such that $L^3$ may or may not be present;

m is 0, 1, or 2;

k is 0 or 1;

R¹ and R² are independently selected from hydrogen, hydrocarbyl, substituted hydrocarbyl, heteroatom-containing hydrocarbyl, substituted heteroatom-containing hydrocarbyl, and functional groups, where R¹ and R² may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and at least one of $R^{V1}$, $R^{V2}$, $R^{V3}$, $R^{V4}$, or $R^{V5}$ is represented by a group such as:

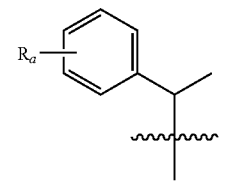

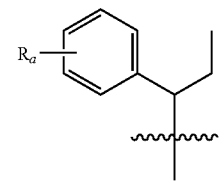

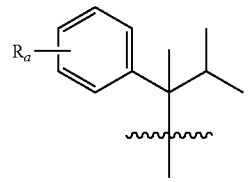

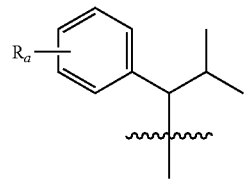

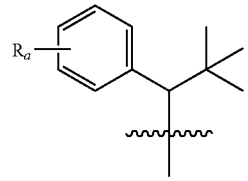

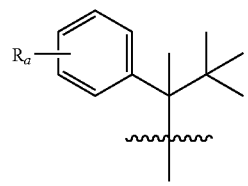

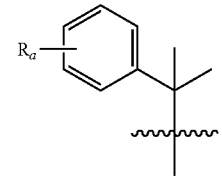

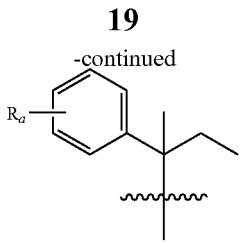

"a" represents 0, 1, 2, 3, 4, or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl, or halogen.

The Group 8 transition metal complex having the structure of Formula (IV) may be in a racemic isomeric form, a meso isomeric form, or a mixture of the racemic and meso isomeric forms.

In another embodiment, metal carbene olefin metathesis catalysts of the invention comprise a Group 8 transition metal complex having the structure of Formula (V):

Formula (V)

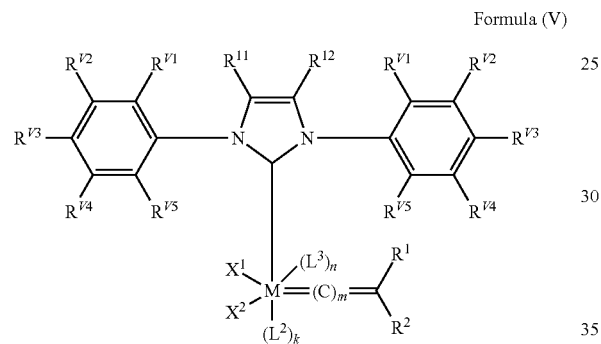

wherein:

M is Ru or Os;

$R^{V1}$, $R^{V2}$, $R^{V3}$, $R^{V4}$, and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, substituted $C_5$-$C_{14}$ aryl;

$R^{11}$ and $R^{12}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide;

$X^1$ and $X^2$ are independently halogen;

$L^2$ and $L^3$ are neutral electron donor ligands, wherein $L^2$ and/or $L^3$ may be linked with $R^1$ or $R^2$ to form one or more cyclic groups;

n is 0 or 1, such that $L^3$ may or may not be present;

m is 0, 1, or 2;

k is 0 or 1;

$R^1$ and $R^2$ are independently selected from hydrogen, hydrocarbyl, substituted hydrocarbyl, heteroatom-containing hydrocarbyl, substituted heteroatom-containing hydrocarbyl, and functional groups, where $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and at least one of $R^{V1}$, $R^{V2}$, $R^{V3}$, $R^{V4}$, or $R^{V5}$ is represented by a group such as:

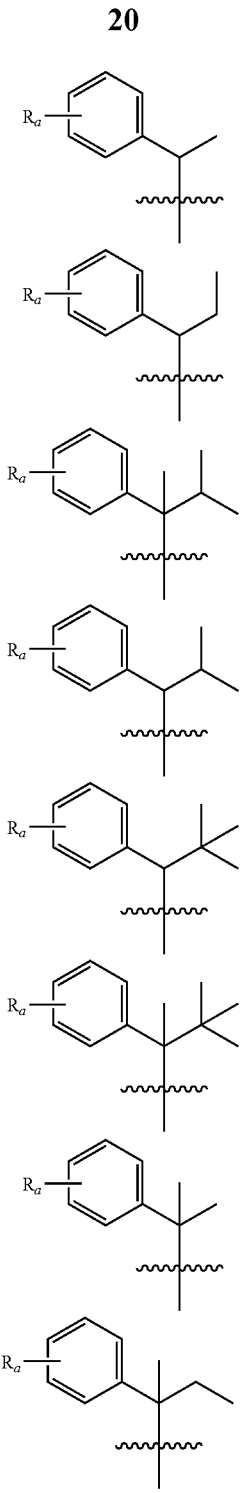

"a" represents 0, 1, 2, 3, 4, or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl, or halogen.

The Group 8 transition metal complex having the structure of Formula (V) may be in a racemic isomeric form, a meso isomeric form, or a mixture of the racemic and meso isomeric forms.

In a second group of catalysts having the structure of Formula (I), wherein M, m, n, $X^1$, $X^2$, $R^1$, and $R^2$ are as defined for the first group of catalysts, $L^1$ is of Formula (II) or of Formula (III) and $L^2$ and $L^3$ are weakly coordinating neutral electron donor ligands in the form of optionally substituted heterocyclic groups. Again, n is zero or 1, such that $L^3$ may or may not be present. Generally, in the second group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the second group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole. Additionally, the nitrogen-containing heterocycles may be optionally substituted on a non-coordinating heteroatom with a non-hydrogen substitutent.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di($C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

Complexes wherein Y is coordinated to the metal are examples of a third group of metal carbene olefin metathesis catalysts, and are commonly called "Grubbs-Hoveyda" catalysts. Grubbs-Hoveyda metathesis-active metal carbene complexes may be described by the Formula (VI):

Formula (VI)

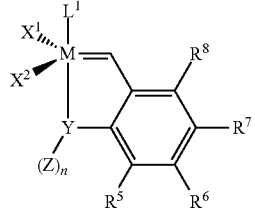

wherein:

M is a Group 8 transition metal, particularly Ru or Os, or, more particularly, Ru;

$L^1$ is of Formula (II) or of Formula (III), and, $X^1$ and $X^2$ are as previously defined herein for the first and second groups of metal carbene olefin metathesis catalysts;

Y is a heteroatom selected from N, O, S, and P; preferably Y is O or N;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkyl sulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein "A" and Fn have been defined above; and any combination of Y, Z, $R^5$, $R^6$, $R^7$, and $R^8$ can be linked to form one or more cyclic groups;

n is 0, 1, or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl. Additionally, $R^5$, $R^6$, $R^7$, $R^8$, and Z may independently be thioisocyanate, cyanato, or thiocyanato.

The Group 8 transition metal complex having the structure of Formula (VI) may be in a racemic isomeric form, a meso isomeric form, or a mixture of the racemic and meso isomeric forms.

In another embodiment, metal carbene olefin metathesis catalysts of the invention comprise a Group 8 transition metal complex having the structure of Formula (VII):

Formula (VII)

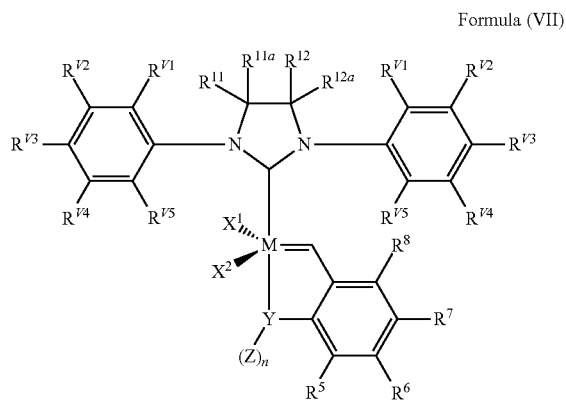

wherein:

M is Ru or Os;

$R^{V1}$, $R^{V2}$, $R^{V3}$, $R^{V4}$, and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, substituted $C_5$-$C_{14}$ aryl;

$R^{11}$, $R^{12}$, $R^{11a}$, and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide;

$X^1$ and $X^2$ are independently halogen;

Y is a heteroatom selected from N, O, S, and P; preferably Y is O or N;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkyl sulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein "A" and Fn have been defined above; and any combination of Y, Z, $R^5$, $R^6$, $R^7$, and $R^8$ can be linked to form one or more cyclic groups;

n is 0, 1, or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and at least one of $R^{V1}$, $R^{V2}$, $R^{V3}$, $R^{V4}$, or $R^{V5}$ is represented by a group such as:

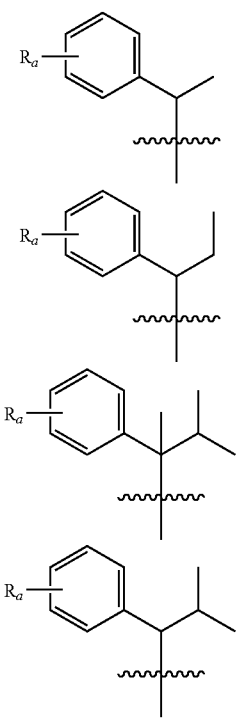

-continued

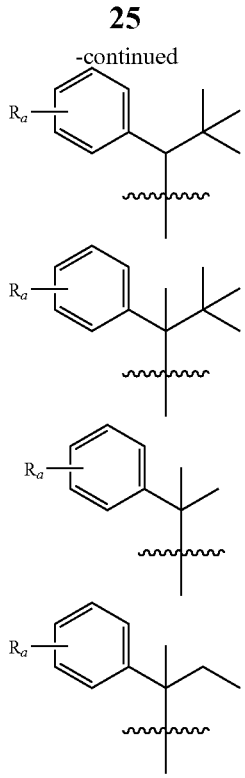

"a" represents 0, 1, 2, 3, 4, or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl, or halogen.

The Group 8 transition metal complex having the structure of Formula (VII) may be in a racemic isomeric form, a meso isomeric form, or a mixture of the racemic and meso isomeric forms.

In another embodiment, metal carbene olefin metathesis catalysts of the invention comprise a Group 8 transition metal complex having the structure of Formula (VII), wherein:

M is Ru;

$R^{V1}$, $R^{V2}$, $R^{V3}$, $R^{V4}$, and $R^{V5}$ are independently hydrogen, substituted branched $C_1$-$C_6$ alkyl;

$R^{11}$, $R^{12}$, $R^{11a}$, and $R^{12a}$ are independently hydrogen, $C_1$-$C_{12}$ alkyl;

$X^1$ and $X^2$ are independently chloride;

Y is O or N;

$R^5$, $R^6$, $R^7$, and $R^8$ are each, independently, selected from the group consisting of hydrogen, halogen, alkyl;

n is 1 or 2; and

Z is a group selected from hydrogen and alkyl; and at least one of $R^{V1}$, $R^{V2}$, $R^{V3}$, $R^{V4}$, or $R^{V5}$ is represented by a group such as:

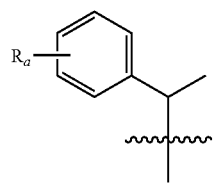

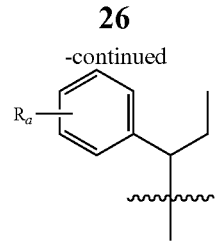
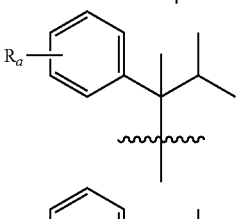
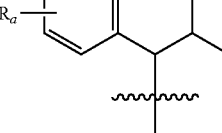
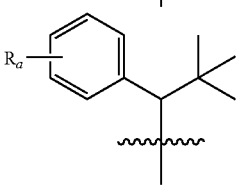
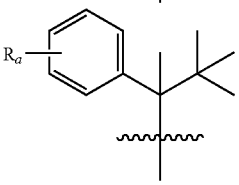
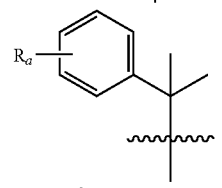
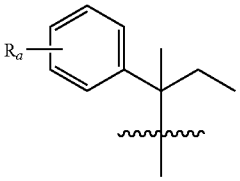

"a" represents 0, 1, 2, 3, 4, or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl, or halogen.

In another embodiment, metal carbene olefin metathesis catalysts of the invention comprise a Group 8 transition metal complex having the structure of Formula (VII):

wherein:

M is Ru;

$R^{V1}$, $R^{V2}$, $R^{V3}$, and $R^{V4}$ are independently hydrogen;

$R^{11}$, $R^{12}$, $R^{11a}$, and $R^{12a}$ are independently hydrogen;

$X^1$ and $X^2$ are independently chloride;

Y is O;

$R^5$, $R^6$, $R^7$, and $R^8$ are each hydrogen;

n is 1;

Z is alkyl;

$R^{V5}$ is represented by

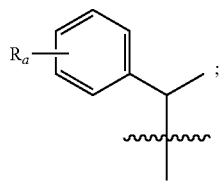

and

"a" represents 0.

Examples of complexes comprising Grubbs-Hoveyda ligands suitable in the invention include:

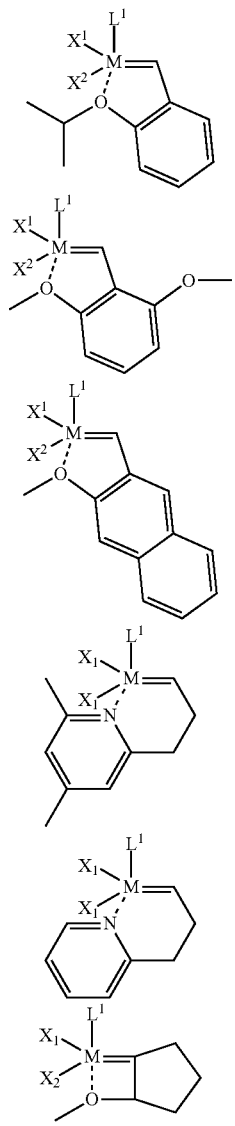

wherein: $L^1$ is of Formula (II) or of Formula (III) and, $X^1$, $X^2$, and M are as described for any of the other groups of catalysts. Suitable chelating carbenes and carbene precursors are further described by Pederson et al. (U.S. Pat. Nos. 7,026,495 and 6,620,955, the disclosures of both of which are incorporated herein by reference) and Hoveyda et al. (U.S. Pat. No. 6,921,735 and WO0214376, the disclosures of both of which are incorporated herein by reference).

In addition to the metal carbene olefin metathesis catalysts that have the structure of Formula (I), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general Formula (VIII);

neutral ruthenium or osmium metal carbene complexes containing metal centers that are formally in the +2 oxidation state, have an electron count of 18, are hexa-coordinated, and are of the general Formula (IX);

cationic ruthenium or osmium metal carbene complexes containing metal centers that are formally in the +2 oxidation state, have an electron count of 14, are tetra-coordinated, and are of the general Formula (X); and cationic ruthenium or osmium metal carbene complexes containing metal centers that are formally in the +2 oxidation state, have an electron count of 14 or 16, are tetra-coordinated or penta-coordinated, respectively, and are of the general Formula (XI):

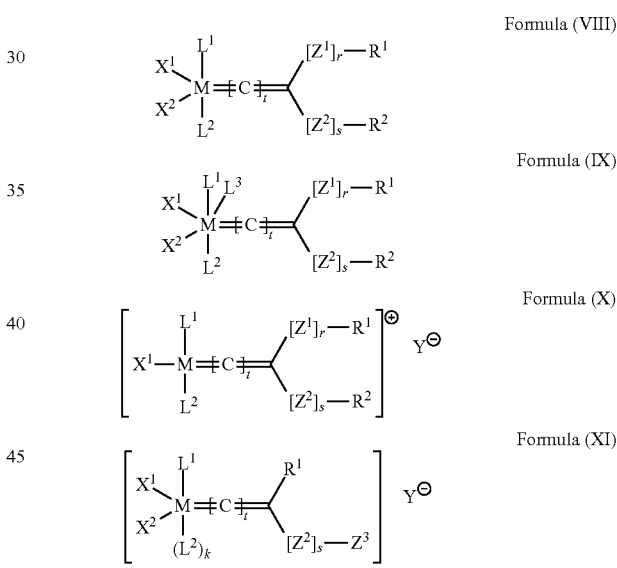

wherein:

M, $X^1$, $X^2$, $L^1$, $L^2$, $L^3$, $R^1$, and $R^2$ are as defined for any of the previously defined groups of catalysts;

r and s are independently 0 or 1;

t is an integer in the range of 0 to 5;

k is an integer in the range of 0 to 1;

Y is any non-coordinating anion (e.g., a halide ion, $BF_4^-$, etc.);

$Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, —S(=O)$_2$—, —, and an optionally substituted and/or optionally heteroatom containing $C_1$-$C_{20}$ hydrocarbylene linkage;

$Z^3$ is any cationic moiety such as —P($R^2$)$_3^+$ or —N($R^2$)$_3^+$; and any two or more of $X^1$, $X^2$, $L^1$, $L^2$, $L^3$, $Z^1$, $Z^2$, $Z^3$, $R^1$, and $R^2$ may be taken together to form a cyclic group, e.g., a multidentate ligand.

The Group 8 transition metal complexes having the structure of Formulae (VIII) to (XI) may be in a racemic isomeric form, a meso isomeric form, or a mixture of the racemic and meso isomeric forms.

Additionally, another group of metal carbene olefin metathesis catalysts that may be used in the invention disclosed herein, is a Group 8 transition metal complex having the structure of Formula (XII):

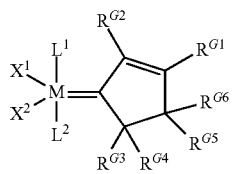

Formula (XII)

wherein: M is a Group 8 transition metal, particularly Ru or Os, or more particularly, Ru; $L^1$ is represented by the structures of Formula (II) or by the structures of Formula (III); $X^1$, $X^2$, and $L^2$ are as defined for the first and second groups of catalysts defined above; and $R^{G1}$, $R^{G2}$, $R^{G3}$, $R^{G4}$, $R^{G5}$, $R^{G6}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkyl sulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{G1}$, $R^{G2}$, $R^{G3}$, $R^{G4}$, $R^{G5}$, and $R^{G6}$ may be linked together to form a cyclic group.

The Group 8 transition metal complex having the structure of Formula (XII) may be in a racemic isomeric form, a meso isomeric form, or a mixture of the racemic and meso isomeric forms.

Additionally, one preferred embodiment of the Group 8 transition metal complex of Formula (XII) is a Group 8 transition metal complex of Formula (XIII)

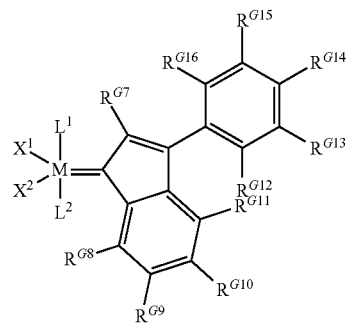

Formula (XIII)

wherein: $L^1$ is represented by the structure of Formula (II) or by the structure of Formula (III); M, $X^1$, $X^2$, and $L^2$ are as defined above for Group 8 transition metal complex of Formula (XII); and $R^{G7}$, $R^{G8}$, $R^{G9}$, $R^{G10}$, $R^{G11}$, $R^{G12}$, $R^{G13}$, $R^{G14}$, $R^{G15}$, and $R^{G16}$ are as defined above for $R^{G1}$, $R^{G2}$, $R^{G3}$, $R^{G4}$, $R^{G5}$, and $R^{G6}$ for Group 8 transition metal complex of Formula (XII) or any one or more of the $R^{G7}$, $R^{G8}$, $R^{G9}$, $R^{G10}$, $R^{G11}$, $R^{G12}$, $R^{G13}$, $R^{G14}$, $R^{G15}$, and $R^{G16}$ may be linked together to form a cyclic group.

The Group 8 transition metal complex having the structure of Formula (XIII) may be in a racemic isomeric form, a meso isomeric form, or a mixture of the racemic and meso isomeric forms.

Additionally, another preferred embodiment of the Group 8 transition metal complex of Formula (XII) is a Group 8 transition metal complex of Formula (XIV):

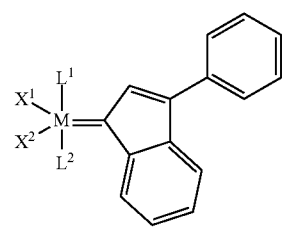

Formula (XIV)

wherein: $L^1$ is represented by Formula (II) or by Formula (III); M, $X^1$, $X^2$, and $L^2$ are as defined above for Group 8 transition metal complex of Formula (XII).

The Group 8 transition metal complex having the structure of Formula (XIV) may be in a racemic isomeric form, a meso isomeric form, or a mixture of the racemic and meso isomeric forms.

Additionally, another group of metal carbene olefin metathesis catalysts that may be used in the invention disclosed herein, is a Group 8 transition metal complex comprising a Schiff base ligand having the structure of Formula (XV):

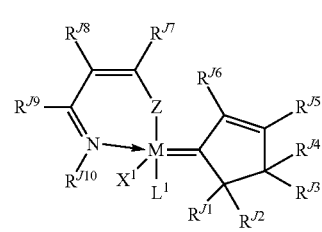

Formula (XV)

wherein:

M is a Group 8 transition metal, particularly Ru or Os, or more particularly, Ru;

$L^1$ is represented by the structure of Formula (II) or by the structure of Formula (III); $X^1$ is as defined for the first and second groups of catalysts defined above;

Z is selected from the group consisting of oxygen, sulfur, selenium, $NR^{J11}$, $PR^{J11}$, $AsR^{J11}$, and $SbR^{J11}$; and $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ may be linked together to form a cyclic group.

The Group 8 transition metal complex having the structure of Formula (XV) may be in a racemic isomeric form, a meso isomeric form, or a mixture of the racemic and meso isomeric forms.

Additionally, another group of metal carbene olefin metathesis catalysts that may be used in the invention disclosed herein, is a Group 8 transition metal complex comprising a Schiff base ligand having the structure of Formula (XVI):

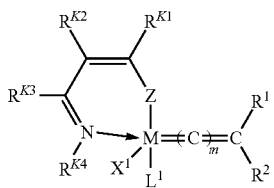

Formula (XVI)

wherein:

M is a Group 8 transition metal, particularly Ru or Os, or more particularly, Ru;

$L^1$ is represented by Formula (II) or by Formula (III); $X^1$, $L^1$, $R^1$, and $R^2$ are as defined for the first and second groups of catalysts defined above;

Z is selected from the group consisting of oxygen, sulfur, selenium, $NR^{K5}$, $PR^{K5}$, $AsR^{K5}$, and $SbR^{K5}$;

m is 0, 1, or 2; and $R^{K1}$, $R^{K2}$, $R^{K3}$, $R^{K4}$, and $R^{K5}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkyl sulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{K1}$, $R^{K2}$, $R^{K3}$, $R^{K4}$, and $R^{K5}$ may be linked together to form a cyclic group.

The Group 8 transition metal complex having the structure of Formula (XVI) may be in a racemic isomeric form, a meso isomeric form, or a mixture of the racemic and meso isomeric forms.

In addition, catalysts of Formulae (XV) and (XVI) may be optionally contacted with an activating compound, where at least partial cleavage of a bond between the Group 8 transition metal and at least one Schiff base ligand occurs, wherein the activating compound is either a metal or silicon compound, inorganic acid, or organic acid.

Examples of preferred metal carbene olefin metathesis catalysts have the structure of Formula (I), wherein:

M is a Group 8 transition metal;

$L^1$ is represented by the structure of Formula (II) or by the structure of Formula (III);

$L^2$ and $L^3$ are neutral electron donor ligands;

n is 0 or 1;

m is 0, 1, or 2;

k is 0 or 1;

$X^1$ and $X^2$ are anionic ligands;

$R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, and $R^2$ can be taken together to form one or more cyclic groups;

$R^{V1}$, $R^{V2}$, $R^{V3}$, $R^{V4}$, and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, substituted $C_5$-$C_{14}$ aryl; and $R^{11}$, $R^{12}$, $R^{11a}$, and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C5$-$C_{14}$ aryl, or halide;

at least one of $R^{V1}$, $R^{V2}$, $R^{V3}$, $R^{V4}$, or $R^{V5}$ is represented by a group such as:

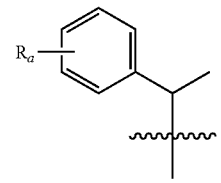

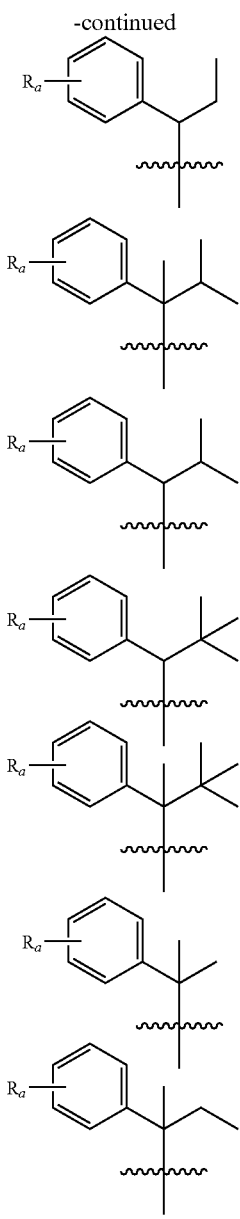

"a" represents 0, 1, 2, 3, 4, or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl, or halogen, wherein the catalyst may be in a racemic isomeric form, a meso isomeric form, or a mixture of the racemic and meso isomeric forms.

Examples of preferred metal carbene olefin metathesis catalysts have the structure of Formula (VI), wherein:

M is Ru or Os;

$L^1$ is represented by the structure of Formula (II) or by the structure of Formula (III);

$X^1$ and $X^2$ are anionic ligands;

Y is a heteroatom selected from O or N;

$R^5$, $R^6$, $R^7$, and $R^8$ are independently selected from hydrogen, hydrocarbyl, substituted hydrocarbyl, heteroatom-containing hydrocarbyl, substituted heteroatom-containing hydrocarbyl, and functional groups;

n is 0, 1, or 2; and

Z is selected from hydrogen, hydrocarbyl, substituted hydrocarbyl, heteroatom-containing hydrocarbyl, substituted heteroatom-containing hydrocarbyl, and functional groups; wherein any combination of Y, Z, $R^5$, $R^6$, $R^7$, and $R^8$ can be linked to form one or more cyclic groups;

$R^{V1}$, $R^{V2}$, $R^{V3}$, $R^{V4}$, and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, substituted $C_5$-$C_{14}$ aryl; and $R^{11}$, $R^{12}$, $R^{11a}$, and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide; at least one of $R^{V1}$, $R^{V2}$, $R^{V3}$, $R^{V4}$, or $R^{V5}$ is represented by a group such as:

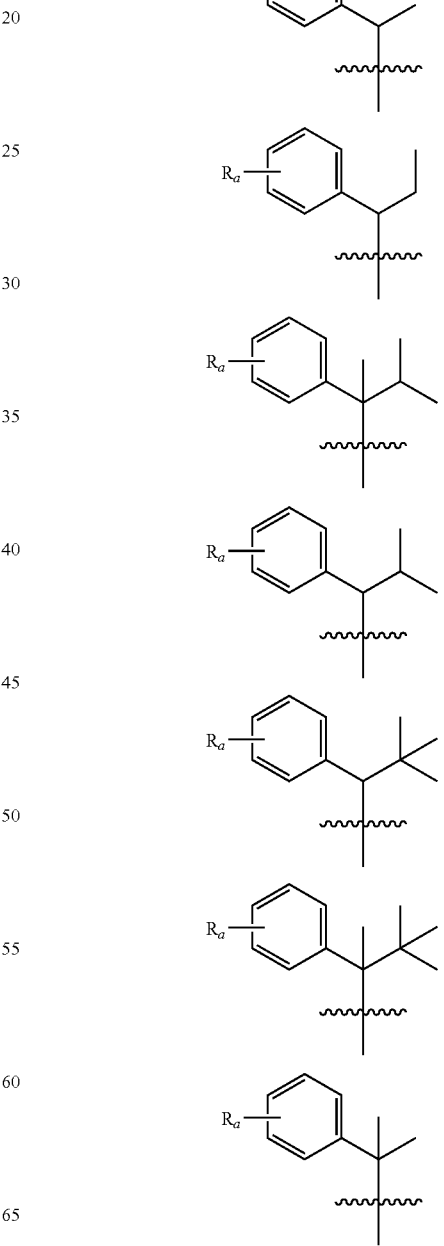

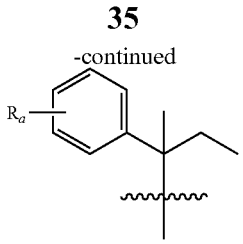

"a" represents 0, 1, 2, 3, 4, or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl or halogen, wherein the catalyst may be in a racemic isomeric form, a meso isomeric form, or a mixture of the racemic and meso isomeric forms.

Examples of preferred metal carbene olefin metathesis catalysts have the structure of Formula (I), wherein:

M is Ru;

n is 0;

m is 0;

k is 1;

$L^1$ is represented by the structure of Formula (II) or by the structure of Formula (III);

$L^2$ is trisubstituted phosphines selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene and $L^2$ is a trisubstituted phosphine selected from the group consisting of tri-n-butylphosphine (Pn-Bu$_3$), tricyclopentylphosphine (PC$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph);

$X^1$ and $X^2$ are chloride;

$R^1$ is hydrogen and $R^2$ is phenyl or —CH=C(CH$_3$)$_2$ or thienyl; or $R^1$ and $R^2$ are taken together to form phenylindenylidene;

$R^{V1}$, $R^{V2}$, $R^{V3}$, $R^{V4}$, and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, substituted $C_5$-$C_{14}$ aryl; and $R^{11}$, $R^{12}$, $R^{11a}$, and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide; at least one of $R^{V1}$, $R^{V2}$, $R^{V3}$, $R^{V4}$, or $R^{V5}$ is represented by a group such as:

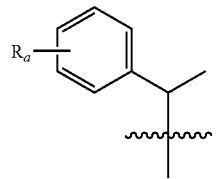

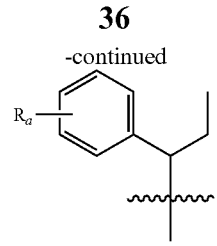

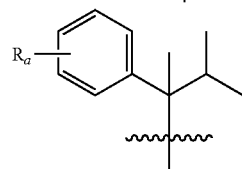

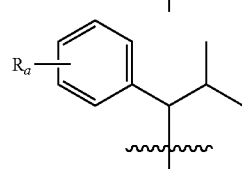

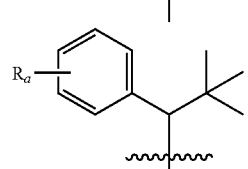

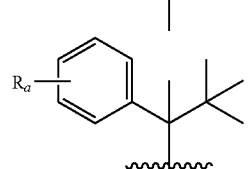

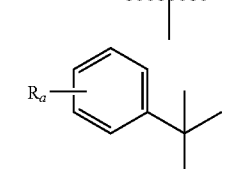

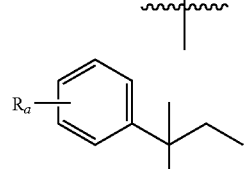

"a" represents 0, 1, 2, 3, 4, or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl, or halogen, wherein the catalyst may be in a racemic isomeric form, a meso isomeric form, or a mixture of the racemic and meso isomeric forms.

Examples of preferred metal carbene olefin metathesis catalysts have the structure of Formula (VI), wherein:

M is Ru;

$L^1$ is represented by the structure of Formula (II) or by the structure of Formula (III);

$X^1$ and $X^2$ are chloride;

Y is oxygen;

$R^5$, $R^6$, $R^7$, and $R^8$ are each hydrogen;

n is 1;

Z is isopropyl;

$R^{V1}$, $R^{V2}$, $R^{V3}$, $R^{V4}$, and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, substituted $C_5$-$C_{14}$ aryl;

$R^{11}$, $R^{12}$, $R^{11a}$, $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide; at least one of $R^{V1}$, $R^{V2}$, $R^{V3}$, $R^4$, or $R^{V5}$ is represented by a group such as:

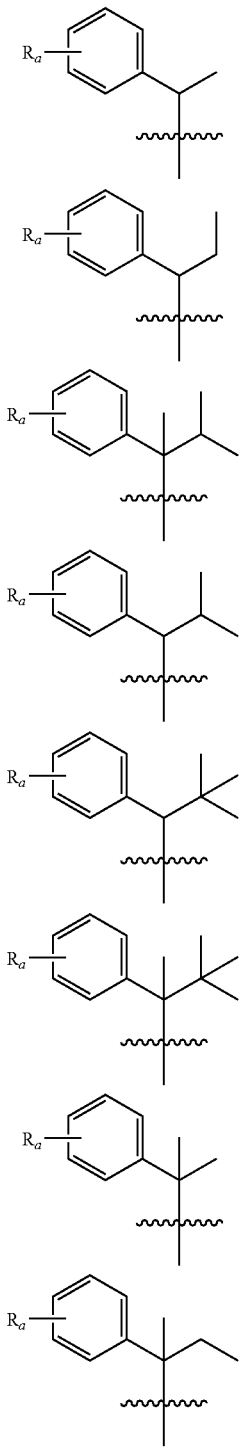

"a" represents 0, 1, 2, 3, 4, or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl, or halogen, wherein the catalyst may be in a racemic isomeric form, a meso isomeric form, or a mixture of the racemic and meso isomeric forms.

Examples of preferred metal carbene olefin metathesis catalysts have the structure of Formula (I), wherein:

M is Ru;
n is 0;
m is 0;
k is 1;
$L^1$ is represented by the structure of Formula (II) or by the structure of Formula (III);
$L^2$ is a trisubstituted phosphine independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph);
$X^1$ and $X^2$ are chloride;
$R^1$ is hydrogen and $R^2$ is phenyl or —CH=C(CH$_3$)$_2$ or thienyl; or $R^1$ and $R^2$ are taken together to form phenylindenylidene;
$R^{V1}$, $R^{V2}$, $R^{V3}$, $R^{V4}$, and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, substituted $C_5$-$C_{14}$ aryl; and
$R^{11}$, $R^{12}$, $R^{11a}$, and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide; at least one of $R^{V1}$, $R^{V2}$, $R^{V3}$, $R^{V4}$, or $R^{V5}$ is represented by a group such as:

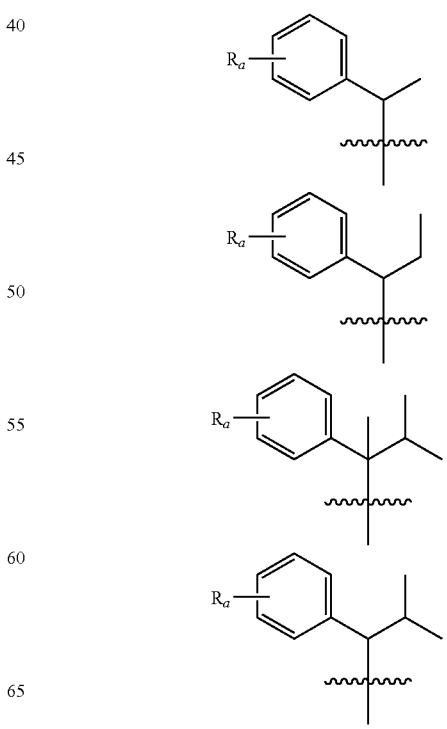

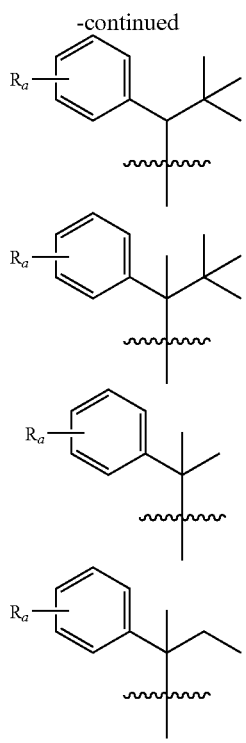

"a" represents 0, 1, 2, 3, 4, or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl, or halogen, wherein the catalyst may be in a racemic isomeric form, a meso isomeric form, or a mixture of the racemic and meso isomeric forms, wherein the catalyst may be in a racemic isomeric form, a meso isomeric form, or a mixture of the racemic and meso isomeric forms.

The catalysts of the invention may be utilized in olefin metathesis reactions according to techniques known in the art. The catalysts of the invention are typically used as a solid, a solution, or as a suspension. When the catalysts of the invention are used as a suspension, the catalysts of the invention are suspended in a dispersing carrier such as mineral oil, paraffin oil, soybean oil, tri-isopropylbenzene, or any hydrophobic liquid which has a sufficiently high viscosity so as to permit effective dispersion of the catalyst(s), and which is sufficiently inert and which has a sufficiently high boiling point so that is does not act as a low-boiling impurity in the olefin metathesis reaction. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate.

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

When expressed as the molar ratio of monomer to catalyst, the catalyst (the "monomer to catalyst ratio"), loading will generally be present in an amount that ranges from a low of about 10,000,000:1, 1,000,000:1, 500,000:1 or 200,00:1, to a high of about 100,000:1 60,000:1, 50,000:1, 45,000:1, 40,000:1, 30,000:1, 20,000:1, 10,000:1, 5,000:1, or 1,000:1.

In one embodiment, the invention provides metal carbene olefin metathesis catalysts of structures:

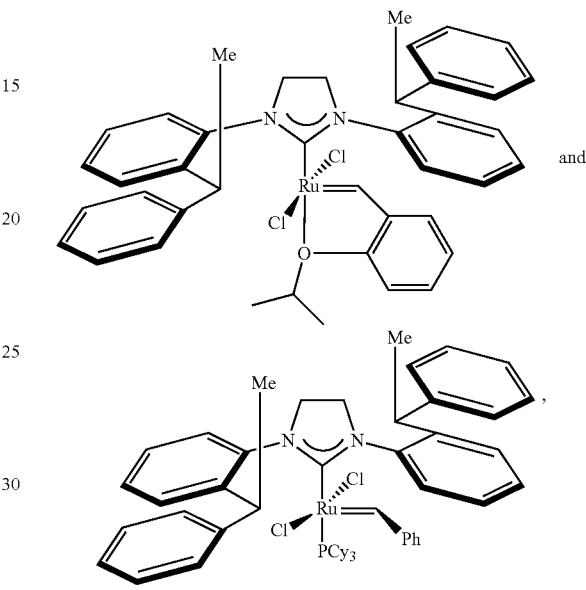

wherein the catalysts may be in a racemic isomeric form, a meso isomeric form, or a mixture of the racemic and meso isomeric forms.

Cyclic Olefins

One or more cyclic olefins may be used with the present invention disclosed herein. In general, any cyclic olefin suitable for the metathesis reactions disclosed herein may be used. Such cyclic olefins may be optionally substituted, optionally heteroatom-containing, mono-unsaturated, di-unsaturated, or poly-unsaturated $C_5$ to $C_{24}$ hydrocarbons that may be mono-, di-, or poly-cyclic. The cyclic olefin may generally be any strained or unstrained cyclic olefin, provided the cyclic olefin is able to participate in a metathesis reaction (e.g., ROMP, ROCM, etc.). While certain unstrained cyclic olefins such as cyclohexene are generally understood to not undergo ROMP reactions by themselves, under appropriate circumstances, such unstrained cyclic olefins may nonetheless be ROMP active. For example, when present as a co-monomer in a ROMP composition, unstrained cyclic olefins may be ROMP active. Accordingly, as used herein and as would be appreciated by the skilled artisan, the term "unstrained cyclic olefin" is intended to refer to those unstrained cyclic olefins that may undergo a ROMP reaction under any conditions, or in any ROMP composition, provided the unstrained cyclic olefin is ROMP active.

In general, the cyclic olefin may be represented by the structure of Formula (A)

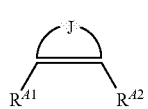

Formula (A)

wherein J, $R^{A1}$, and $R^{A2}$ are as follows: $R^{A1}$ and $R^{A2}$ is selected independently from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkyl sulfanyl, $C_5$-$C_{20}$ aryl sulfanyl, $C_1$-$C_{20}$ alkyl sulfonyl, $C_5$-$C_{20}$ aryl sulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge). $R^{A1}$ and $R^{A2}$ may itself be one of the aforementioned groups, such that the Fn moiety is directly bound to the olefinic carbon atom indicated in the structure. In the latter case, however, the functional group will generally not be directly bound to the olefinic carbon through a heteroatom containing one or more lone pairs of electrons, e.g., an oxygen, sulfur, nitrogen, or phosphorus atom, or through an electron-rich metal or metalloid such as Ge, Sn, As, Sb, Se, Te, etc. With such functional groups, there will normally be an intervening linkage Z*, such that $R^{A1}$ and/or $R^{A2}$ then has the structure —$(Z^*)_n$-Fn wherein n is 1, Fn is the functional group, and Z* is a hydrocarbylene linking group such as an alkylene, substituted alkylene, heteroalkylene, substituted heteroalkene, arylene, substituted arylene, heteroarylene, or substituted heteroarylene linkage. J is a saturated or unsaturated hydrocarbylene, substituted hydrocarbylene, heteroatom-containing hydrocarbylene, or substituted heteroatom-containing hydrocarbylene linkage, wherein when J is substituted hydrocarbylene or substituted heteroatom-containing hydrocarbylene, the substituents may include one or more —$(Z^*)_n$-Fn groups, wherein n is 0 or 1, and Fn and Z* are as defined previously. Additionally, two or more substituents attached to ring carbon (or other) atoms within J may be linked to form a bicyclic or polycyclic olefin. J will generally contain in the range of approximately 5 to 14 ring atoms, typically 5 to 8 ring atoms, for a monocyclic olefin, and, for bicyclic and polycyclic olefins, each ring will generally contain 4 to 8, typically 5 to 7, ring atoms.

Mono-unsaturated cyclic olefins encompassed by Formula (A) may be represented by the Formula (B):

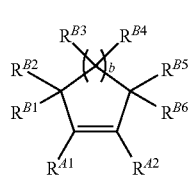

Formula (B)

wherein b is an integer generally although not necessarily in the range of 1 to 10, typically 1 to 5, $R^{A1}$ and $R^{A2}$ are as defined above for Formula (A), and $R^{B1}$, $R^{B2}$, $R^{B3}$, $R^{B4}$, $R^{B5}$, and $R^{B6}$ are independently selected from the group consisting of hydrogen, hydrocarbyl, substituted hydrocarbyl, heteroatom-containing hydrocarbyl, substituted heteroatom-containing hydrocarbyl and —$(Z^*)_n$-Fn where n, Z* and Fn are as defined previously, and wherein if any of the $R^{B1}$ through $R^{B6}$ moieties is substituted hydrocarbyl or substituted heteroatom-containing hydrocarbyl, the substituents may include one or more —$(Z^*)_n$-Fn groups. Accordingly, $R^{B1}$, $R^{B2}$, $R^{B3}$, $R^{B4}$, $R^{B5}$, and $R^{B6}$ may be, for example, hydrogen, hydroxyl, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_2$-$C_{24}$ alkylcarbonyloxy, $C_5$-$C_{20}$ aryloxycarbonyl, amino, amido, nitro, etc.

Furthermore, any of the $R^{B1}$, $R^{B2}$, $R^{B3}$, $R^{B4}$, $R^{B5}$, and $R^{B6}$ moieties can be linked to any of the other $R^{B1}$, $R^{B2}$, $R^{B3}$, $R^{B4}$, $R^{B5}$, and $R^{B6}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is 0 or 1, Z* and Fn are as defined previously, and functional groups (Fn) provided above.

Examples of monounsaturated, monocyclic olefins encompassed by Formula (B) include, without limitation, cyclopentene, cyclohexene, cycloheptene, cyclooctene, cyclononene, cyclodecene, cycloundecene, cyclododecene, tricyclodecene, tetracyclodecene, octacyclodecene, and cycloeicosene, and substituted versions thereof such as 1-methylcyclopentene, 1-ethylcyclopentene, 1-isopropylcyclohexene, 1-chloropentene, 1-fluorocyclopentene, 4-methylcyclopentene, 4-methoxy-cyclopentene, 4-ethoxy-cyclopentene, cyclopent-3-ene-thiol, cyclopent-3-ene, 4-methylsulfanyl-cyclopentene, 3-methylcyclohexene, 1-methylclocooctene, 1,5-dimethylcyclooctene, etc.

Monocyclic diene reactants encompassed by Formula (A) may be generally represented by the Formula (C):

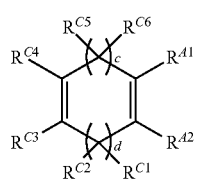

Formula (C)

wherein c and d are independently integers in the range of 1 to about 8, typically 2 to 4, preferably 2 (such that the reactant is a cyclooctadiene), $R^{A1}$ and $R^{A2}$ are as defined above for Formula (A) and $R^{C1}$, $R^{C2}$, $R^{C3}$, $R^{C4}$, $R^{C5}$, and $R^{C6}$ are defined as for $R^{B1}$ through $R^{B6}$. In this case, it is preferred that $R^{C3}$ and $R^{C4}$ be non-hydrogen substituents, in which case the second olefinic moiety is tetrasubstituted. Examples of monocyclic diene reactants include, without limitation, 1,3-cyclopentadiene, 1,3-cyclohexadiene, 1,4-cyclohexadiene, 5-ethyl-1,3-cyclohexadiene, 1,3-cycloheptadiene, cyclohepatadiene, 1,5-cyclooctadiene, 1,3-cyclooctadiene, and substituted analogs thereof. Triene reactants are analogous to the diene Formula (C), and will generally contain at least one methylene linkage between any two olefinic segments.

Bicyclic and polycyclic olefins encompassed by Formula (A) may be generally represented by the Formula (D):

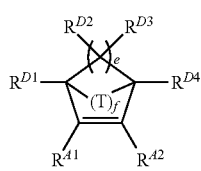

Formula (D)

wherein $R^{A1}$ and $R^{A2}$ are as defined above for Formula (A), $R^{D1}$, $R^{D2}$, $R^{D3}$, and $R^{D4}$ are as defined for $R^{B1}$ through $R^{B6}$, e is an integer in the range of 1 to 8 (typically 2 to 4), f is generally 1 or 2; T is lower alkylene or alkenylene (generally substituted or unsubstituted methyl or ethyl), $CHR^{G1}$, $C(R^{G1})_2$, O, S, N—$R^{G1}$, P—$R^{G1}$, O=P—$R^{G1}$, $Si(R^{G1})_2$, B—$R^{G1}$, or As—$R^{G1}$ where $R^{G1}$ is alkyl, alkenyl, cycloalkyl, cycloalkenyl, aryl, alkaryl, aralkyl, or alkoxy. Furthermore, any of the $R^{D1}$, $R^{D2}$, $R^{D3}$, and $R^{D4}$ moieties can be linked to any of the other $R^{D1}$, $R^{D2}$, $R^{D3}$, and $R^{D4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multi substitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is 0 or 1, $Z^*$ and Fn are as defined previously, and functional groups (Fn) provided above.

Cyclic olefins encompassed by Formula (D) are in the norbornene family. As used herein, norbornene means any compound that includes at least one norbornene or substituted norbornene moiety, including without limitation norbornene, substituted norbornene(s), norbornadiene, substituted norbornadiene(s), polycyclic norbornenes, and substituted polycyclic norbornene(s). Norbornenes within this group may be generally represented by the Formula (E):

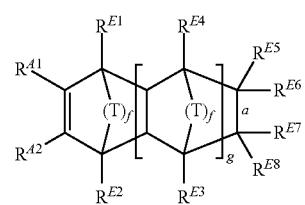

Formula (E)

wherein $R^{A1}$ and $R^{A2}$ are as defined above for Formula (A), T is as defined above for Formula (D) $R^{E1}$, $R^{E2}$, $R^{E3}$, $R^{E4}$, $R^{E5}$, $R^{E6}$, $R^{E7}$, and $R^{E8}$ are as defined for $R^{B1}$ through $R^{B6}$, and "a" represents a single bond or a double bond, f is generally 1 or 2, "g" is an integer from 0 to 5, and when "a" is a double bond one of $R^{E5}$, $R^{E6}$ and one of $R^{E7}$, $R^{E8}$ is not present.

Furthermore, any of the $R^{E5}$, $R^{E6}$, $R^{E7}$, and $R^{E8}$ moieties can be linked to any of the other $R^{E5}$, $R^{E6}$, $R^{E7}$, and $R^{E8}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is 0 or 1, $Z^*$ and Fn are as defined previously, and functional groups (Fn) provided above.

More preferred cyclic olefins possessing at least one norbornene moiety have the Formula (F):

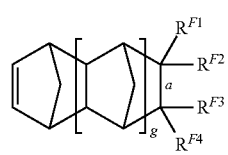

Formula (F)

wherein $R^{F1}$, $R^{F2}$, $R^{F3}$, and $R^{F4}$, are as defined for $R^{B1}$ through $R^{B6}$, and "a" represents a single bond or a double bond, "g" is an integer from 0 to 5, and when "a" is a double bond one of $R^{F1}$, $R^{F2}$ and one of $R^{F3}$, $R^{F4}$ is not present.

Furthermore, any of the $R^{F1}$, $R^{F2}$, $R^{F3}$, and $R^{F4}$ moieties can be linked to any of the other $R^{F1}$, $R^{F2}$, $R^{F3}$, and $R^{F4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain mono-substitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is 0 or 1, $Z^*$ and Fn are as defined previously, and functional groups (Fn) provided above.

Examples of bicyclic and polycyclic olefins thus include, without limitation, dicyclopentadiene (DCPD); trimer and other higher order oligomers of cyclopentadiene including without limitation tricyclopentadiene (cyclopentadiene trimer), cyclopentadiene tetramer (tetracyclopentadiene), and cyclopentadiene pentamer (pentacyclopentadiene); ethylidenenorbornene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethyoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5,6-dimethoxycarbonylnorbornene; endo, endo-5,6-dimethoxycarbonylnorbornene; 2,3-dimethoxynorbornene; norbornadiene; tricycloundecene; tetracyclododecene; 8-methyltetracyclododecene; 8-ethyltetracyclododecene; 8-methoxycarbonyltetracyclododecene; 8-methyl-8-tetracyclododecene; 8-cyanotetracyclododecene; pentacyclopentadecene; pentacyclohexadecene; and the like, and their structural isomers, stereoisomers, and mixtures thereof. Additional examples of bicyclic and polycyclic olefins include, without limitation, $C_2$-$C_{12}$ hydrocarbyl substituted norbornenes such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, and 5-butenyl-2-norbornene, and the like. It is well understood by one of skill in the art that bicyclic and polycyclic olefins as disclosed herein may consist of a variety of structural isomers and/or stereoisomers, any and all of which are suitable for use in the present invention. Any reference herein to such bicyclic and polycyclic olefins unless specifically stated includes mixtures of any and all such structural isomers and/or stereoisomers.

Preferred cyclic olefins include $C_5$ to $C_{24}$ unsaturated hydrocarbons. Also preferred are $C_5$ to $C_{24}$ cyclic hydrocarbons that contain one or more (typically 2 to 12) heteroatoms such as O, N, S, or P. For example, crown ether cyclic olefins may include numerous O heteroatoms throughout the cycle, and these are within the scope of the invention. In addition, preferred cyclic olefins are $C_5$ to $C_{24}$ hydrocarbons that contain one or more (typically 2 or 3) olefins. For example, the cyclic olefin may be mono-, di-, or tri-unsaturated. Examples of cyclic olefins include without limitation cyclooctene, cyclododecene, and (c,t,t)-1,5,9-cyclododecatriene.

The cyclic olefins may also comprise multiple (typically 2 or 3) rings. For example, the cyclic olefin may be mono-, di-, or tri-cyclic. When the cyclic olefin comprises more than one ring, the rings may or may not be fused. Preferred examples of cyclic olefins that comprise multiple rings include norbornene, dicyclopentadiene, tricyclopentadiene, and 5-ethylidene-2-norbornene.

The cyclic olefin may also be substituted, for example, a $C_5$ to $C_{24}$ cyclic hydrocarbon wherein one or more (typically 2, 3, 4, or 5) of the hydrogens are replaced with non-hydrogen substituents. Suitable non-hydrogen substituents may be chosen from the substituents described hereinabove. For example, functionalized cyclic olefins, i.e., $C_5$ to $C_{24}$ cyclic hydrocarbons wherein one or more (typically 2, 3, 4, or 5) of the hydrogens are replaced with functional groups, are within the scope of the invention. Suitable functional groups may be chosen from the functional groups described hereinabove. For example, a cyclic olefin functionalized with an alcohol group may be used to prepare a telechelic polymer comprising pendent alcohol groups. Functional groups on the cyclic olefin may be protected in cases where the functional group interferes with the metathesis catalyst, and any of the protecting groups commonly used in the art may be employed. Acceptable protecting groups may be found, for example, in Greene et al., Protective Groups in Organic Synthesis, 3rd Ed. (New York: Wiley, 1999). Examples of functionalized cyclic olefins include without limitation 2-hydroxymethyl-5-norbornene, 2-[(2-hydroxyethyl)carboxylate]-5-norbornene, cydecanol, 5-n-hexyl-2-norbornene, 5-n-butyl-2-norbornene.

Cyclic olefins incorporating any combination of the abovementioned features (i.e., heteroatoms, substituents, multiple olefins, multiple rings) are suitable for the methods disclosed herein. Additionally, cyclic olefins incorporating any combination of the abovementioned features (i.e., heteroatoms, substituents, multiple olefins, multiple rings) are suitable for the invention disclosed herein.

The cyclic olefins useful in the methods disclosed herein may be strained or unstrained. It will be appreciated that the amount of ring strain varies for each cyclic olefin compound, and depends upon a number of factors including the size of the ring, the presence and identity of substituents, and the presence of multiple rings. Ring strain is one factor in determining the reactivity of a molecule towards ring opening olefin metathesis reactions. Highly strained cyclic olefins, such as certain bicyclic compounds, readily undergo ring opening reactions with olefin metathesis catalysts. Less strained cyclic olefins, such as certain unsubstituted hydrocarbon monocyclic olefins, are generally less reactive. In some cases, ring opening reactions of relatively unstrained (and therefore relatively unreactive) cyclic olefins may become possible when performed in the presence of the olefinic compounds disclosed herein. Additionally, cyclic olefins useful in the invention disclosed herein may be strained or unstrained.

A plurality of cyclic olefins may be used to prepare metathesis polymers from the olefinic compound. For example, two cyclic olefins selected from the cyclic olefins described hereinabove may be employed in order to form metathesis products that incorporate both cyclic olefins. Where two or more cyclic olefins are used, one example of a second cyclic olefin is a cyclic alkenol, i.e., a $C_5$-$C_{24}$ cyclic hydrocarbon wherein at least one of the hydrogen substituents is replaced with an alcohol or protected alcohol moiety to yield a functionalized cyclic olefin.

The use of a plurality of cyclic olefins, and in particular when at least one of the cyclic olefins is functionalized, allows for further control over the positioning of functional groups within the products. For example, the density of cross-linking points can be controlled in polymers and macromonomers prepared using the methods disclosed herein. Control over the quantity and density of substituents and functional groups also allows for control over the physical properties (e.g., melting point, tensile strength, glass transition temperature, etc.) of the products. Control over these and other properties is possible for reactions using only a single cyclic olefin, but it will be appreciated that the use of a plurality of cyclic olefins further enhances the range of possible metathesis products and polymers formed.

Examples of cyclic olefins include dicyclopentadiene; tricyclopentadiene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethoxycarbonyl-1-norbornene; 5-methyl-5-methoxy-carbonylnorbornene; 5-cyanonorbornene; 5,5,6-trimethyl-2-norbornene; cyclo-hexenylnorbornene; exo-5,6-dimethoxynorbornene; endo, endo-5,6-dimethoxynorbornene; endo, exo-5-6-dimethoxycarbonylnorbornene; endo, endo-5,6-dimethoxycarbonylnorbornene; 2,3-dimethoxynorbornene; norbornadiene; tricycloundecene; tetracyclododecene; 8-methyltetracyclododecene; 8-ethyl-tetracyclododecene; 8-methoxycarbonyltetracyclododecene; 8-methyl-8-tetracyclo-dodecene; 8-cyanotetracyclododecene; pentacyclopentadecene; pentacyclohexadecene; higher order oligomers of cyclopentadiene such as cyclopentadiene tetramer, cyclopentadiene pentamer, and the like; and $C_2$-$C_{12}$ hydrocarbyl substituted norbornenes such as 5-butyl-2-norbornene; 5-hexyl-2-norbornene; 5-octyl-2-norbornene; 5-decyl-2-norbornene; 5-dodecyl-2-norbornene; 5-vinyl-2-norbornene; 5-ethylidene-2-norbornene; 5-isopropenyl-2-norbornene; 5-propenyl-2-norbornene; and 5-butenyl-2-norbornene, and the like. Examples of cyclic olefins include dicyclopentadiene, tricyclopentadiene, and higher order oligomers of cyclopentadiene, such as cyclopentadiene tetramer, cyclopentadiene pentamer, and the like, tetracyclododecene, norbornene, and $C_2$-$C_{12}$ hydrocarbyl substituted norbornenes, such as 5-butyl-2-norbornene, 5-hexyl-2-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene, and the like. Examples of cyclic olefins include dicyclopentadiene, tricyclopentadiene, and higher order oligomers of cyclopentadiene, such as cyclopentadiene tetramer, cyclopentadiene pentamer, and the like, tetracyclododecene, norbornene, and $C_2$-$C_{12}$ hydrocarbyl substituted norbornenes, such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene, and the like. Examples of cyclic olefins include dicyclopentadiene, tricyclopentadiene, and higher order oligomers of cyclopentadiene, such as cyclopentadiene tetramer, cyclopentadiene pentamer, and the like, including structural isomers and/or stereoisomers, any and all of which are suitable for use in the present invention. Examples of cyclic olefins include dicyclopentadiene, tricyclopentadiene, and tetracyclopentadiene, including structural isomers and/or stereoisomers, any and all of which are suitable for use in the present invention. Examples of cyclic olefins include dicyclopentadiene and tricyclopentadiene, including structural isomers and/or stereoisomers, any and all of which are suitable for use in the present invention.

Acyclic olefins suitable for use in the invention, include but are not limited to non-substituted or substituted internal olefins, non-substituted or substituted terminal olefins, or non-substituted or substituted terminal dienes, where the substituents are selected from hydrocarbyl, substituted hydrocarbyl, heteroatom-containing hydrocarbyl, substituted heteroatom-containing hydrocarbyl, and functional groups. Acyclic olefins for use in the invention may contain monounsaturation or multiunsaturation.

Olefin Reactant Comprising a Reactant Terminal Olefin

In one example an olefin reactant comprising a reactant terminal olefin may be represented by the structure of Formula (G):

Formula (G)

wherein $D^1$ and $D^2$ are independently selected from nil, $CH_2$, O, or S; and $E^1$ and $E^2$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^{31}$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—N═C═O), thioisocyanate (—N═C═S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkyl sulfanyl (—S-alkyl; also termed "alkylthio"), $C_5$-$C_{24}$ aryl sulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkyl sulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

One or more olefin reactants comprising a reactant terminal olefin may be used with the invention described herein, wherein the one or more olefin reactants comprising a reactant terminal olefin may be the same or different.

Olefin Reactant Comprising a Reactant Internal Olefin

One or more olefin reactants comprising a reactant internal olefin may be used with the invention described herein, wherein the one or more olefin reactants comprising a reactant internal olefin may be the same or different.

In the one or more olefin reactants comprising a reactant internal olefin, the reactant internal olefin may be in the (Z)- or (E)-configuration. In one embodiment, in the one or more olefin reactants comprising a reactant internal olefin, the reactant internal olefin is in the (Z)-configuration. In one embodiment, in the one or more olefin reactants comprising a reactant internal olefin, the reactant internal olefin is in the (E)-configuration.

In one example an olefin reactant comprising a reactant internal olefin may be represented by the structure of Formula (H):

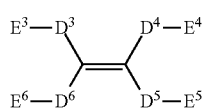

Formula (H)

wherein $D^3$, $D^4$, $D^5$, and $D^6$ are independently selected from nil, CH$_2$, O, or S; and $E^3$, $E^4$, $E^5$, and $E^6$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N (alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Olefin Reactant Comprising Two Terminal Olefins

One or more olefin reactants comprising a reactant olefin may be used with the invention described herein, wherein the olefin reactant comprises two terminal olefins (i.e., a diene) wherein the olefin reactant is brought into contact in the presence of a catalytically effective amount of the metal carbene olefin metathesis catalyst, under conditions and for a time period effective to allow the cross metathesis reaction to occur.

An example of an olefin reactant comprising two terminal olefins (i.e., a diene) is a diene represented by the structure of Formula (J):

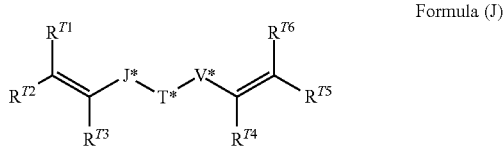

Formula (J)

wherein:

$J^*$ and $V^*$ are independently selected from $C_1$-$C_{20}$ alkylene and substituted $C_1$-$C_{20}$ alkylene; $T^*$ is selected from nil, carbonyl (—C=O), carboxyl (—C(O)—O—), carbamoyl (—C(O)—NH—) and amino (—NH—), or —C($R^{T7}$)($R^{T8}$)—; $R^{T1}$, $R^{T2}$, $R^{T3}$, $R^{T4}$, $R^{T5}$, $R^{T6}$, $R^{T7}$, and $R^{T8}$ are independently selected from hydrogen, hydrocarbyl (e.g., $C_1$-$C_{20}$ alkyl, $C_5$-$C_{24}$ aryl, $C_6$-$C_{24}$ alkaryl, $C_6$-$C_{24}$ aralkyl), substituted hydrocarbyl (e.g., substituted $C_1$-$C_{20}$ alkyl, $C_5$-$C_{24}$ aryl, $C_6$-$C_{24}$ alkaryl, $C_6$-$C_{24}$ aralkyl), heteroatom-containing hydrocarbyl (e.g., heteroatom-containing $C_1$-$C_{20}$ alkyl, $C_5$-$C_{24}$ aryl, $C_6$-$C_{24}$ alkaryl, $C_6$-$C_{24}$ aralkyl), and substituted heteroatom-containing hydrocarbyl (e.g., substituted heteroatom-containing $C_1$-$C_{20}$ alkyl, $C_5$-$C_{24}$ aryl, $C_6$-$C_{24}$ alkaryl, $C_6$-$C_{24}$ aralkyl), and functional groups, wherein the substituent groups are selected from functional groups selected from the group consisting of halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl); $R^{T1}$, $R^{T2}$, $R^{T3}$, $R^{T4}$, $R^{T5}$, $R^{T6}$, $R^{T7}$, $R^{T8}$, and functional groups cannot contain olefinic carbon-carbon double bonds (i.e., —C=C—) or carbon-carbon triple bonds (i.e., —C≡C—).

Any two of $R^{T1}$, $R^{T2}$, $R^{T3}$, $R^{T4}$, $R^{T5}$, $R^{T6}$, $R^{T7}$, and $R^{T8}$ may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C=C—) or carbon-carbon triple bonds (i.e., —C≡C—).

It is to be understood that while the invention has been described in conjunction with specific embodiments thereof, that the description above as well as the examples that follow are intended to illustrate and not limit the scope of the invention. Other aspects, advantages, and modifications within the scope of the invention will be apparent to those skilled in the art to which the invention pertains.

EXAMPLES

The following examples are for illustrative purposes only and are not intended, nor should they be construed as limiting the invention in any manner. Those skilled in the art will appreciate that variations and modifications of the following examples can be made without exceeding the spirit or scope of the invention.

All reactions involving metal complexes were conducted in oven-dried glassware under an argon or nitrogen atmosphere using standard Schlenk techniques. Chemicals and solvents were obtained from Sigma-Aldrich, Strem, Afla Aesar, Nexeo, Brenntag, AG Layne and TCI. Commercially available reagents were used as received unless otherwise noted. Silica gel was purchased from Fisher (0.040-0.063 μm, EMD Millipore).

Cyclic olefin metathesis catalysts were prepared by standard methods and include: [1,3-bis[2-(1-methylethyl)phenyl]-2-imidazolidinylidene]dichloro(phenylmethylene) (tricyclohexylphosphine) Ruthenium(II) (C849); [1,3-bis-(2,4,6-trimethyl phenyl)-2-imidazolidinylidene] dichloro (phenylmethylene) (tricyclohexyl phosphine) Ruthenium(II) (C848); dichloro(phenylmethylene) bis(tricyclohexylphosphine) Ruthenium(II) (C823); dichloro(2-(1-methylethoxy) phenyl]methylene) (tricyclohexylphosphine) Ruthenium(II) (C601).

$^1$H and $^{13}$C NMR spectra were recorded.

Volatile products were analyzed using an Agilent 6850 gas chromatography (GC) instrument with a flame ionization detector (FID). The following conditions and equipment were used:

Column: HP-5, 30 m×0.25 mm (ID)×0.25 μm film thickness.
Manufacturer: Agilent
GC conditions: Injector temperature: 250° C.
Detector temperature: 280° C.
Oven temperature: Starting temperature: 100° C., hold time: 1 minute.
Ramp rate 10° C./min to 250° C., hold time: 12 minutes.
Carrier gas: Helium
Mean gas velocity: 31.3±3.5% cm/sec (calculated)
Split ratio: ~50:1

The products were characterized by comparing peaks with known standards, in conjunction with supporting data from mass spectrum analysis (GCMS-Agilent 5973N). GCMS analysis was accomplished with a second HP-5, 30 m×0.25 mm (ID)×0.25 μm film thickness GC column, using the same method as above.

The following abbreviations are used in the examples and throughout the specification:

| | |
|---|---|
| DCM/CH$_2$Cl$_2$ | dichloromethane |
| rt | room temperature |
| CDCl$_3$ | deuterated chloroform |
| CD$_2$Cl$_2$ | deuterated dichloromethane |
| C$_6$D$_6$ | deuterated benzene |
| C$_6$H$_6$ | benzene |

C848

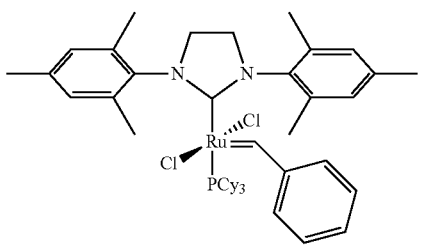

[1,3-bis-(2,4,6-trimethylphenyl)-2-imidazolidinylidene]dichloro(phenylmethylene)(tricyclohexylphosphine) Ruthenium(II) CAS [246047-72-3]

C849

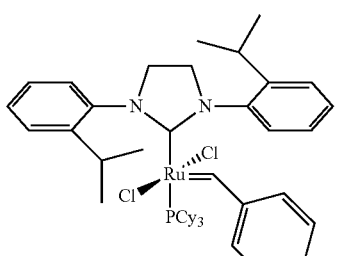

[1,3-bis[2-(1-methylethyl)phenyl]-2-imidazolidinylidene]dichloro(phenylmethylene)(tricyclohexylphosphine) Ruthenium(II) CAS [936715-64-9]

C823

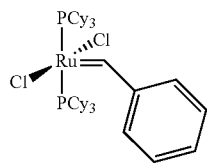

dichloro(phenylmethylene) bis(tricyclohexylphosphine) Ruthenium(II) CAS [172222-30-9]

C601

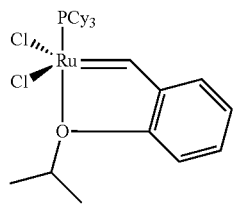

dichloro(2-(1-methylethoxy)phenyl]methylene) (tricyclohexylphosphine) Ruthenium(II) CAS [203714-71-0]

| | |
|---|---|
| Cy | cyclohexyl |
| RCM | ring closing metathesis |
| ROCM | ring opening cross metathesis |
| ROMP | ring opening metathesis polymerization |
| CM | cross metathesis |
| NHC | N-heterocyclic carbene |
| min | minutes |
| gas chromatography | GC |
| PPh$_3$MeBr | methyltriphenylphosphonium bromide |
| NaH | sodium hydride |
| Pd/C | palladium on carbon |
| H$_2$ | hydrogen |
| Al(OPh)$_3$ | tri-phenoxy aluminum |
| NaBH$_4$ | sodium borohydride |
| c-HCl | concentrated hydrochloride acid |
| HC(OEt)$_3$ | tri-ethylorthoformate |
| NH$_4$BF$_4$ | ammonium tetrafluoroborate |
| KOtBu | potassium tert-butoxide |
| [Me$_3$Si]$_2$NK | potassium bis(trimethylsilyl)azide |
| DBB | 1,4-dibenzoyloxy-2-butene |
| BTBB | 1,4-bis(triisopropylbenzoyloxy)-2-butene |
| C$_6$H$_6$ | benzene |
| C$_6$D$_6$ | deuterated benzene |
| rac | racemic |

The following experimental methods illustrate how compounds according to the invention were made. Those skilled in the art will routinely be able to modify and/or adapt the following methods to synthesize any compound of the invention.

Example 1

The Synthesis of Catalysts

Example 1a

The Synthesis of Catalyst (3)-Rac

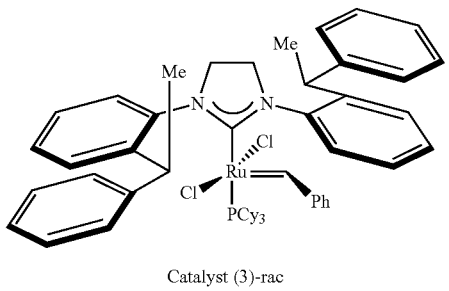

Catalyst (3)-rac

The synthesis of catalyst (3)-rac is shown in Scheme 4. ortho-Phenethylaniline (5) was prepared either through Friedel-Craft reaction from aniline, or Wittig reaction/reduction from compound (4). Condensation of two molecules of (5) with glyoxal, followed by borohydride reduction produced the bis-amine (6) as a mixture of meso and racemic isomers. After separation of the two isomers by column chromatography on silica-gel, crystal structures of both products were obtained to solve their relative stereochemistry. We first chose the racemic isomer of bis-amine amine (6) as NHC ligand, due its $C_2$ symmetry and its steric effects, which would predict the formation of the (E) isomer in our model. Cyclization of (6)-rac provided the NHC salt (7)-rac in high yield. Due to the sterics on ligand (7)-rac, NHC salt, the ligand exchange on catalyst C823 (1) took a long time to complete (6 h at 50° C.), however, catalyst (3)-rac was successfully obtained in high yield (71%) and high purity after chromatography on neutral silica-gel or neutral alumina.

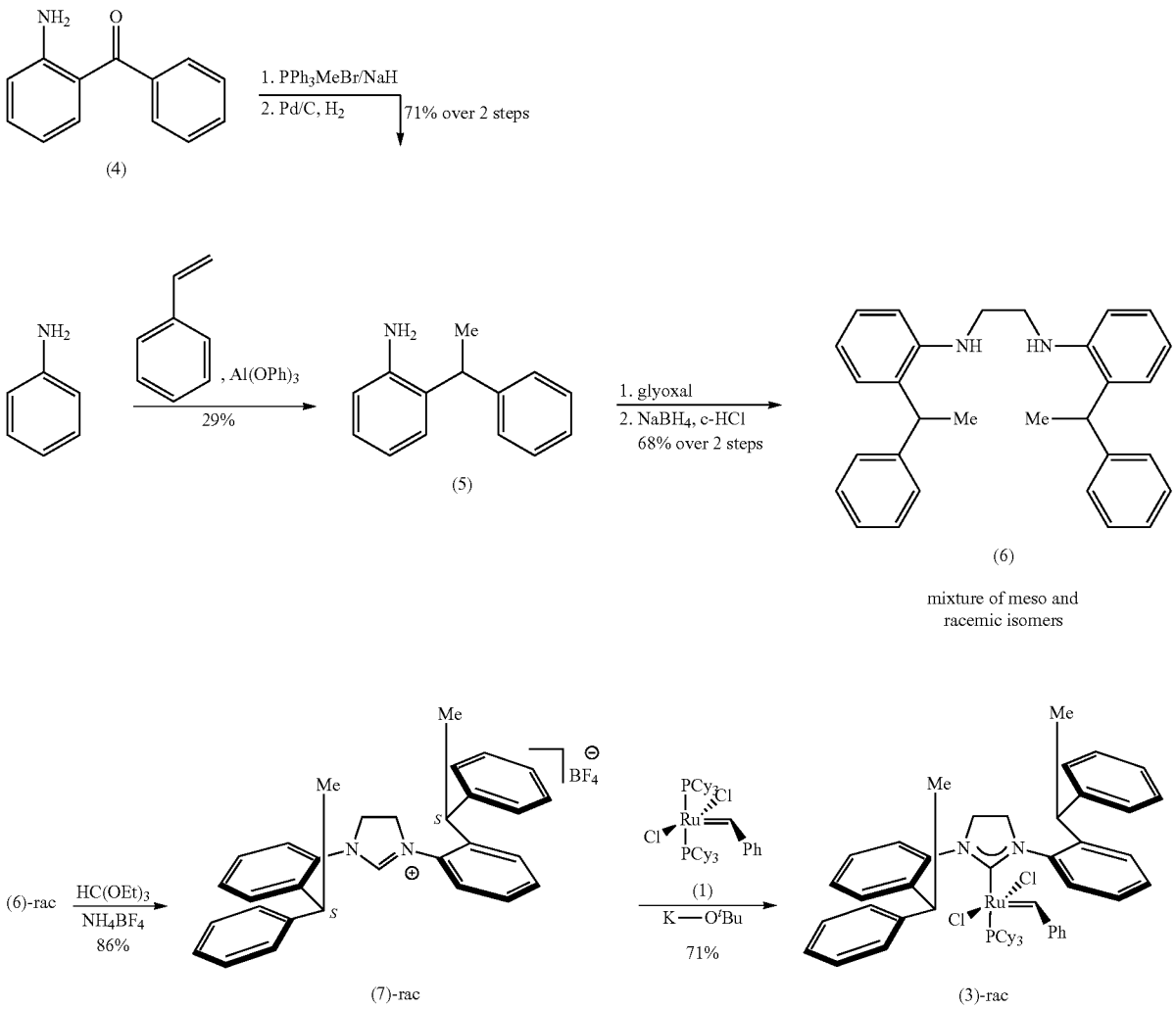

Scheme 4: Synthesis of ruthenium catalyst (3)-rac

Catalyst (3)-meso was synthesized according to the procedure used for the synthesis of Catalyst (3)-rac, using the meso isomer of the NHC-ligand (7).

Example 1b

The Synthesis of Catalyst (16)

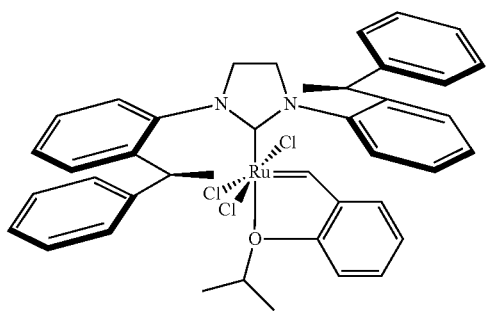

Catalyst (16)-rac

Figure 9:
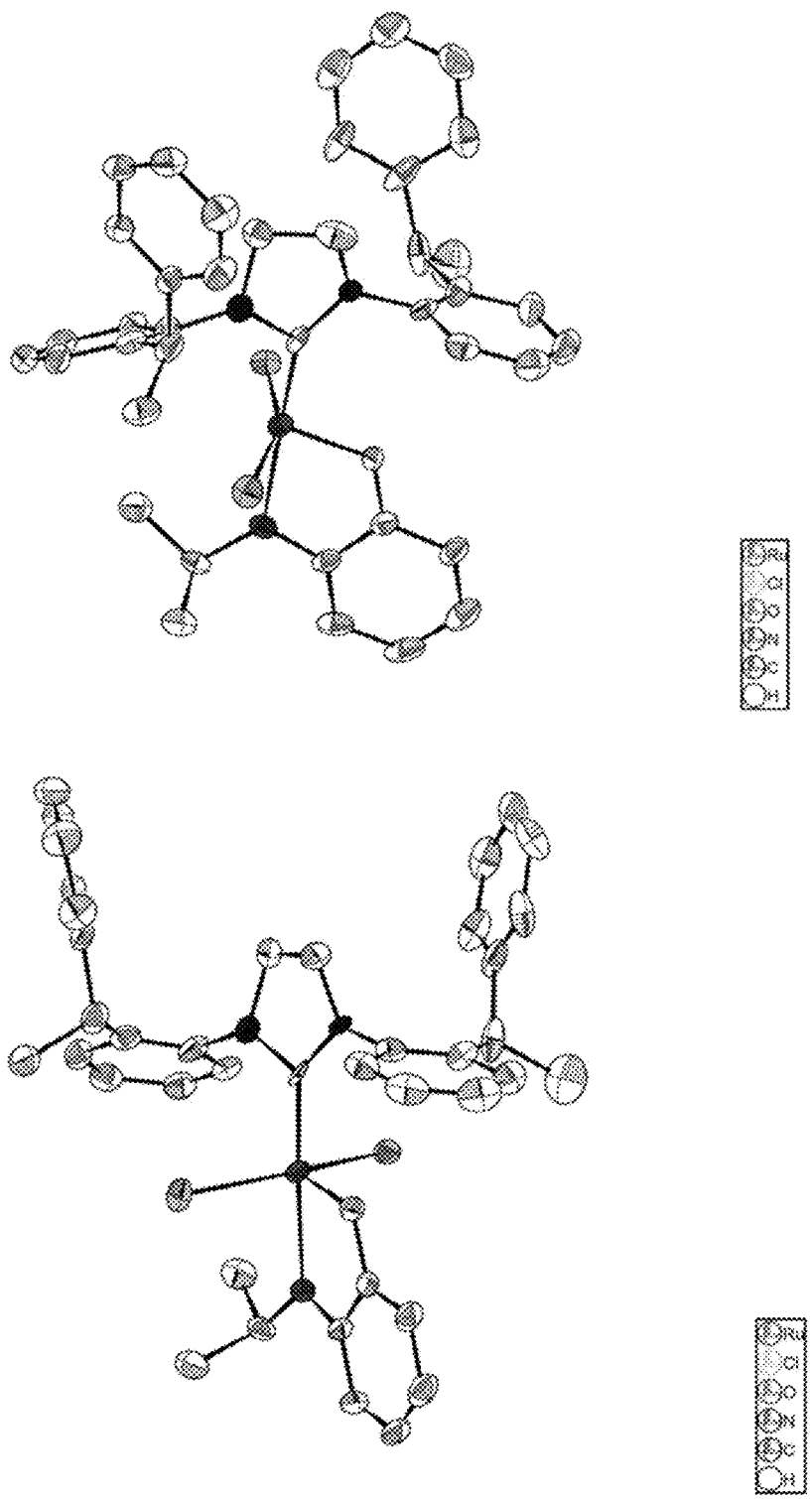
FIG. 9 shows the X-ray crystal structure of catalyst (16)-rac. The crystal structure is shown with 50% probability ellipsoids. Hydrogens are omitted for clarity. Two different orientations of the molecule are shown due to disorder over several atoms.
Figure 10:
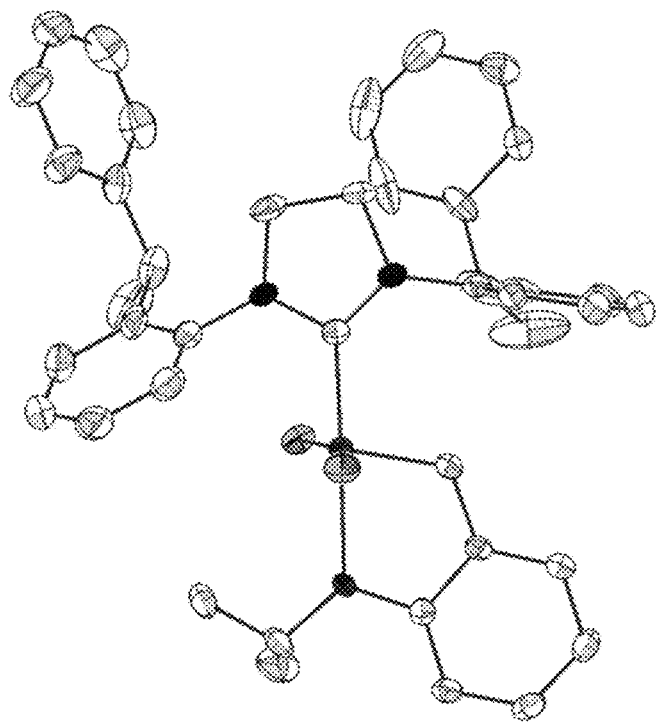
FIG. 10 shows the X-ray crystal structure of catalyst (16)-meso.

The synthesis of catalyst (16)-rac is shown in Scheme 5. Reaction of catalyst C601 (15) with NHC ligand (7)-rac (1.1 equivalents) in the presence of KOtBu (1.1 equivalents) in $C_6H_6$, followed by removal of the solvent under vacuum and purification through column chromatography on silica using dichloromethane as the eluent, yielded catalyst (16)-rac as a green solid. X-ray crystallography (FIG. 9), was used to confirm the structure of this catalyst. The ortho-substituents of the N-aryl groups are oriented such that the NHC ligand bound to the catalyst gave a pseudo-$C_2$-symmetry. One N-aryl group lies directly over the Ru=C bond and lies almost perpendicular to the plane of the aryl group of the benzylidene moiety.

Scheme 5: Synthesis of ruthenium catalyst (16)-rac

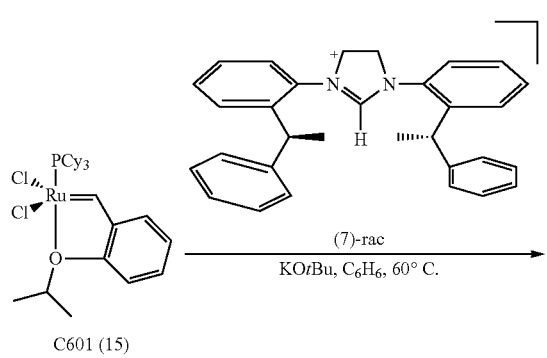

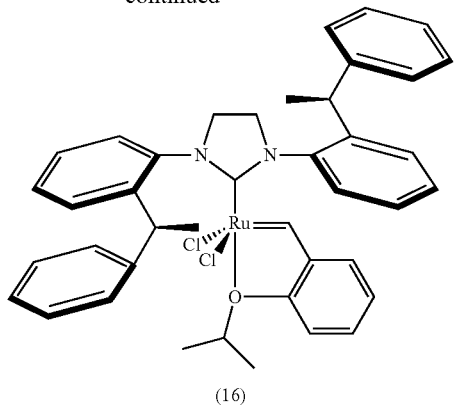

(16)

Catalyst (16)-meso was synthesized according to the procedure used for the synthesis of Catalyst (16)-rac, using the meso isomer of the NHC-ligand (7).

Example 2

Ring Closing Metathesis Reactions

Example 2a

Synthesis of Cyclopentene (9)

The ring closing metathesis activity of new ruthenium complex (3)-rac, was demonstrated with diethyl diallylmalonate (8). An efficient RCM reaction occurred yielding cyclopentene (9) in quantitate yield (Scheme 6).

Scheme 6: Ring closing metathesis catalyzed by (3)-rac

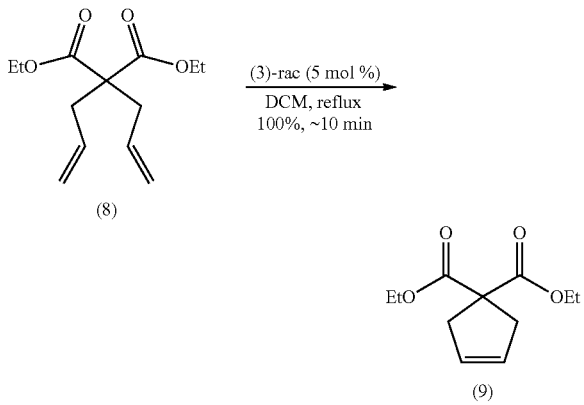

Figure 5:
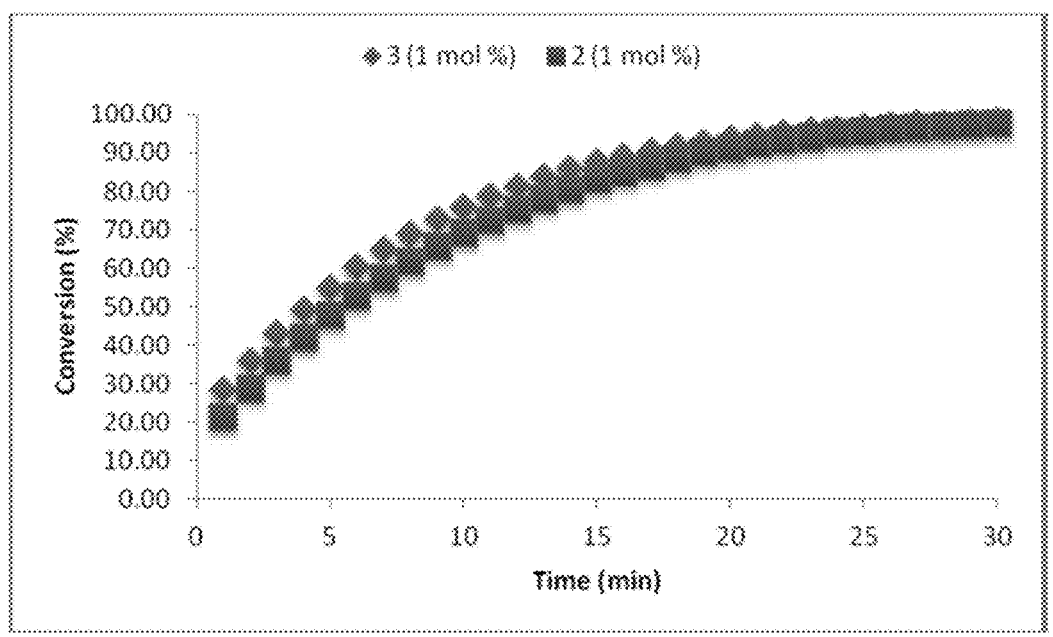
FIG. 5 summarizes the conversion to product (9) of the RCM reaction of Example 2a shown in Scheme 6, using catalyst C848 (2) and catalyst (3)-rac.
Figure 6:
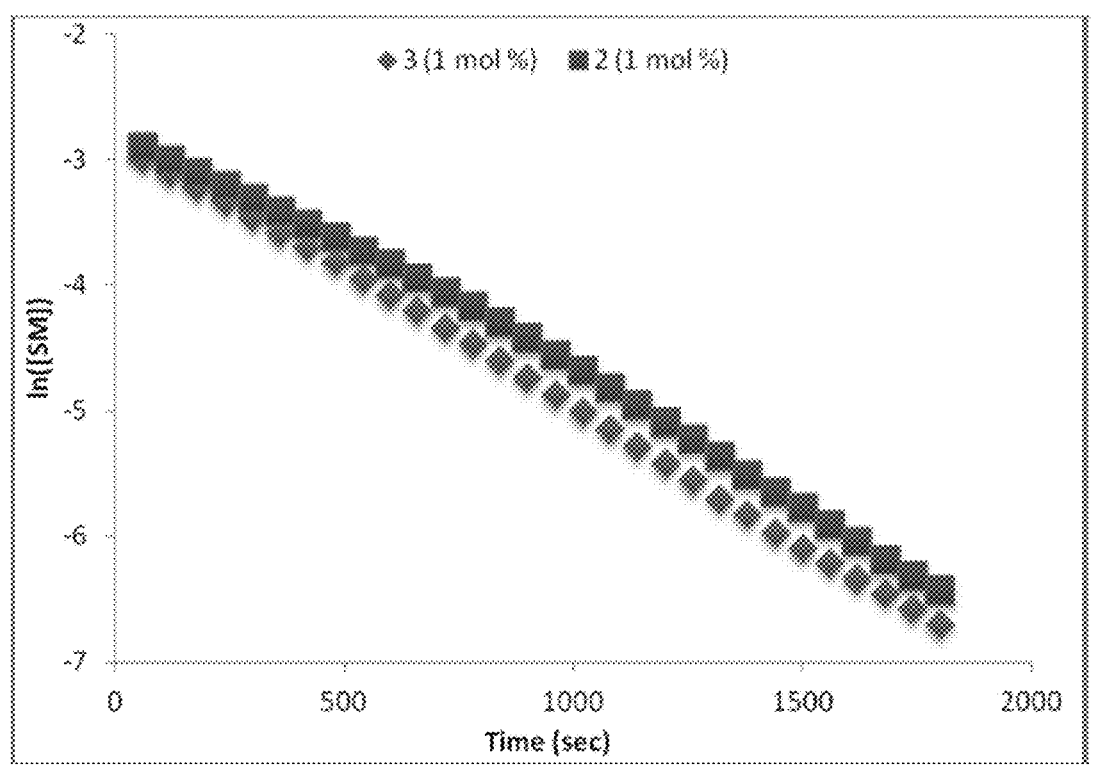
FIG. 6 summarizes the Log plots for catalyst C848 (2) and catalyst (3)-rac in the RCM reaction of Example 2a as shown in Scheme 6.

We also studied the kinetics of catalyst (3)-rac by $^1$H-NMR in the RCM reaction of (8). As shown in FIG. 5, C848 (2) and catalyst (3)-rac have nearly identical activity profiles. Moreover, the logarithmic plot (FIG. 6) is linear, indicating pseudo-first-order kinetics over the course of the reaction. A curvature in the logarithmic plot would be consistent with catalyst decomposition.

Example 2b

Macrocyclic Ring Closing Metathesis Catalyzed by (3)-Rac

The ability of new ruthenium complex (3)-rac was compared with $2^{nd}$ generation catalyst C848 (2) in the macrocyclic ring closing olefin metathesis of diene (10) (Scheme 7). Monitoring the reaction progress by gas chromatography (GC) before 100% conversion was critical to establish the reaction's kinetic profile. In the presence of new ruthenium complex (3)-rac, the reaction yields RCM product (11) with an (E/Z) ratio of 13:1 at 80% conversion while $2^{nd}$ generation catalyst C848 (2) provides an (E/Z) ratio of 10:1 at 84% conversion. The result indicated that new ruthenium complex (3)-rac is slightly more in favor to provide (E)-selective macrocyclic RCM products than (2).

Scheme 7

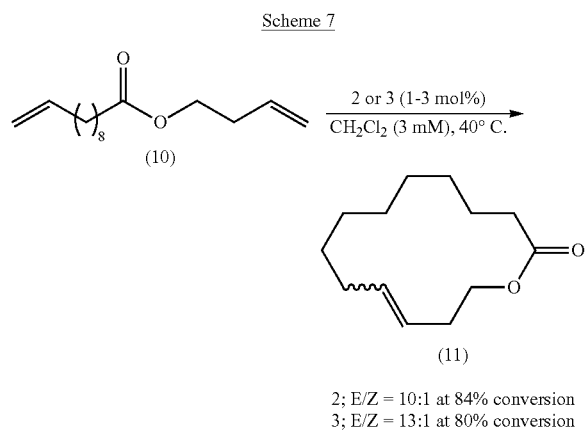

2; E/Z = 10:1 at 84% conversion
3; E/Z = 13:1 at 80% conversion

Example 3

Ring Opening Cross Metathesis Reactions (ROCM) and Ring Opening Metathesis Polymerization Reactions (ROMP)

Example 3a

Ring Opening Cross Metathesis of Norbornene Diacetate (12) with Styrene

Evaluating the (E/Z) selectivity at early conversion is critical since it provides direct insight to kinetic selectivity. We compared the ROCM of norbornene diacetate (12) with styrene in the presence of catalysts C848 (2) and catalyst (3)-rac (Scheme 8).

Scheme 8: ROCM of norbornene diacetate (12) with styrene using C848 (2) and catalyst (3)-rac

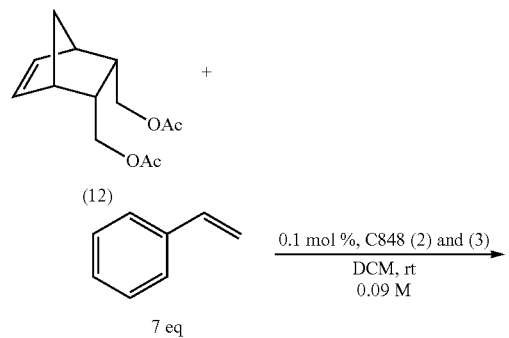

-continued

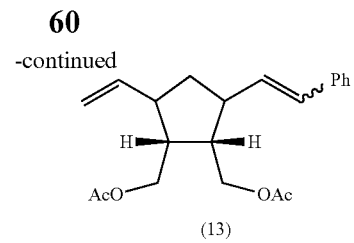

(13)

Figure 2:
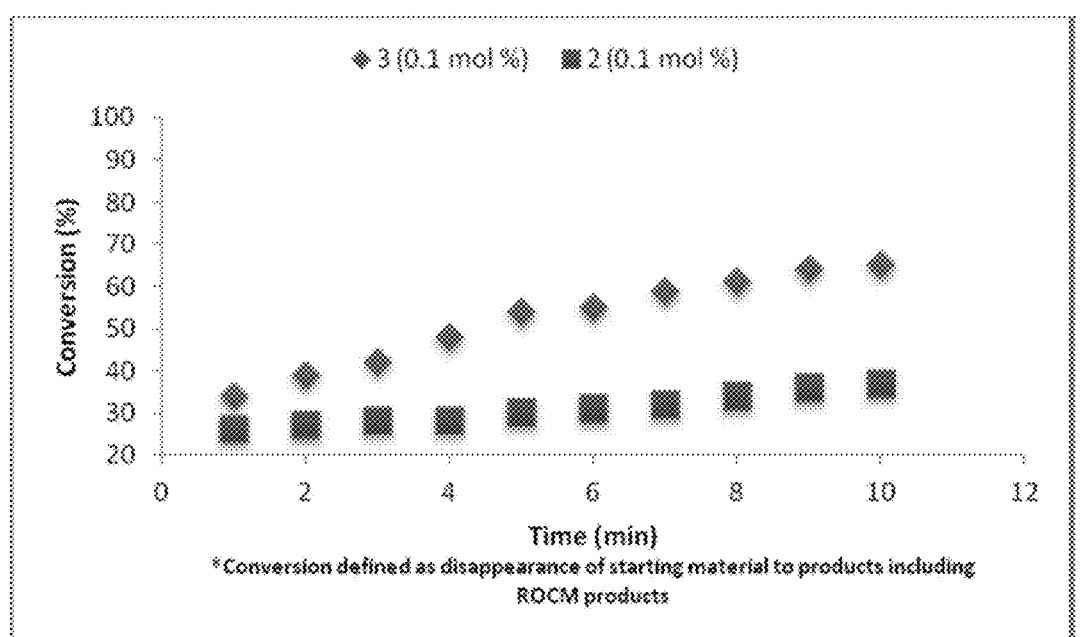
FIG. 2 summarizes the progress of the reaction of Example 3a; ROCM reaction of norbornene (12) to product (13) as shown in Scheme 8, using catalyst C848 (2) and catalyst (3)-rac.
Figure 3:
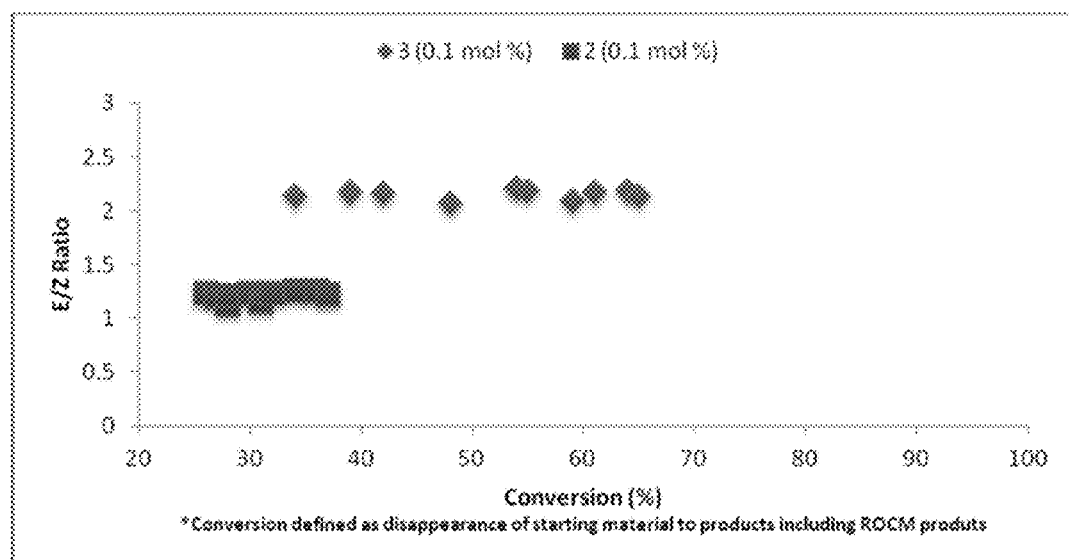
FIG. 3 summarizes the (E/Z) selectivity of product (13) versus conversion, of Example 3a as shown in Scheme 8, using catalyst C848 (2) and catalyst (3)-rac.
Figure 4:
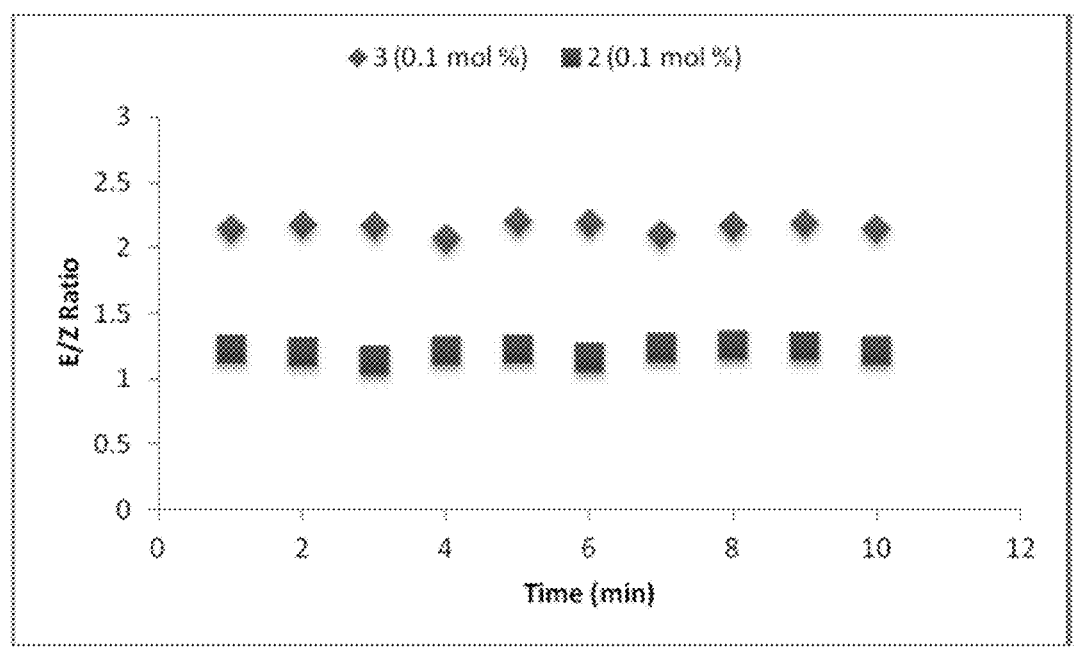
FIG. 4 summarizes the (E/Z) selectivity of product (13) versus time, of Example 3a as shown in Scheme 8, using catalyst C848 (2) and catalyst (3)-rac.

The evolution of the reaction described in Scheme 8 was monitored by GC. The results are shown in FIGS. 2, 3, and 4. FIGS. 2, 3, and 4 summarize the results for the two catalysts examined: C848 (2) and catalyst (3)-rac. In FIG. 2, the chosen reaction conditions provide a reaction environment where the reaction progress can be efficiently monitored. As illustrated in FIG. 3, at 36% conversion, C848 (2) shows an (E/Z) selectivity of 1.2/1. In comparison, at 34% conversion, catalyst (3)-rac shows an (E/Z) selectivity of 2.1:1.

A comparison of selectivity versus time is shown in FIG. 4. For catalyst C848 (2) and catalyst (3)-rac, the (E/Z) ratio remains constant throughout the course of the reaction. This is an indication that catalyst (3)-rac is kinetically more selective than C848 (2) for the (E) form of the ROCM product (13). Thus, a 100% increase in selectivity has been achieved.

Example 3b

Ring Opening Metathesis Polymerization of Cyclooctene With Styrene

Scheme 9: ROMP of cyclooctene with styrene using C848 (2) and catalyst (3)-rac

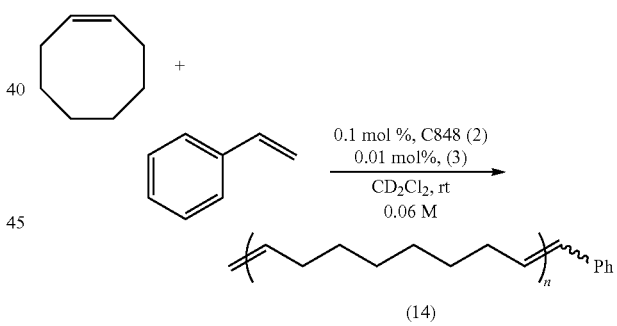

Figure 7:
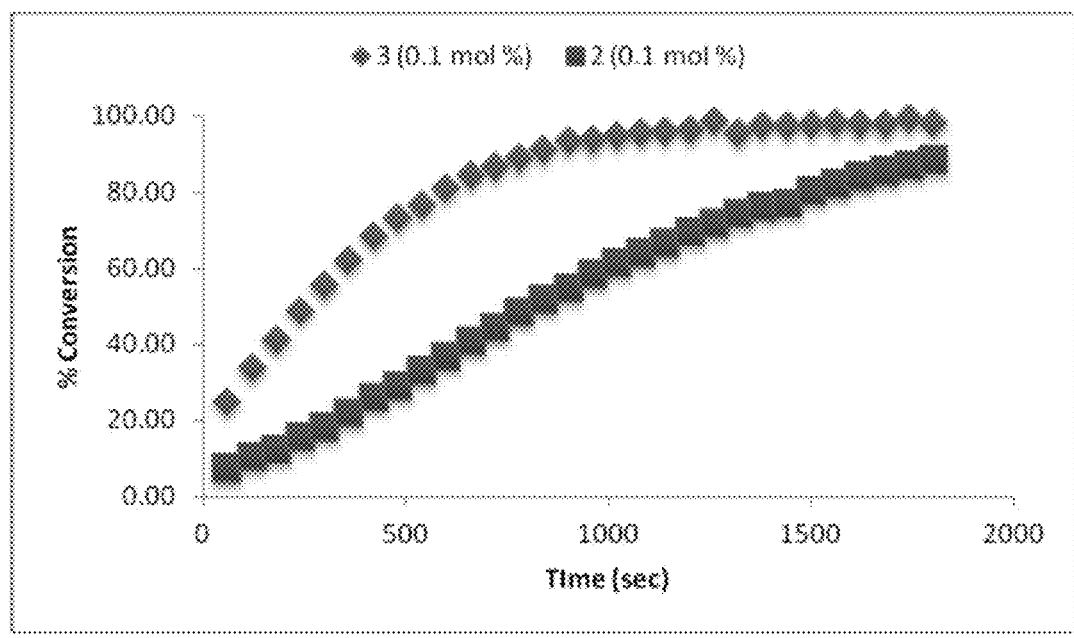
FIG. 7 summarizes the conversion in ROMP reaction of cyclooctene in Example 3b as shown in Scheme 9, using catalyst C848 (2) and catalyst (3)-rac.
Figure 8:
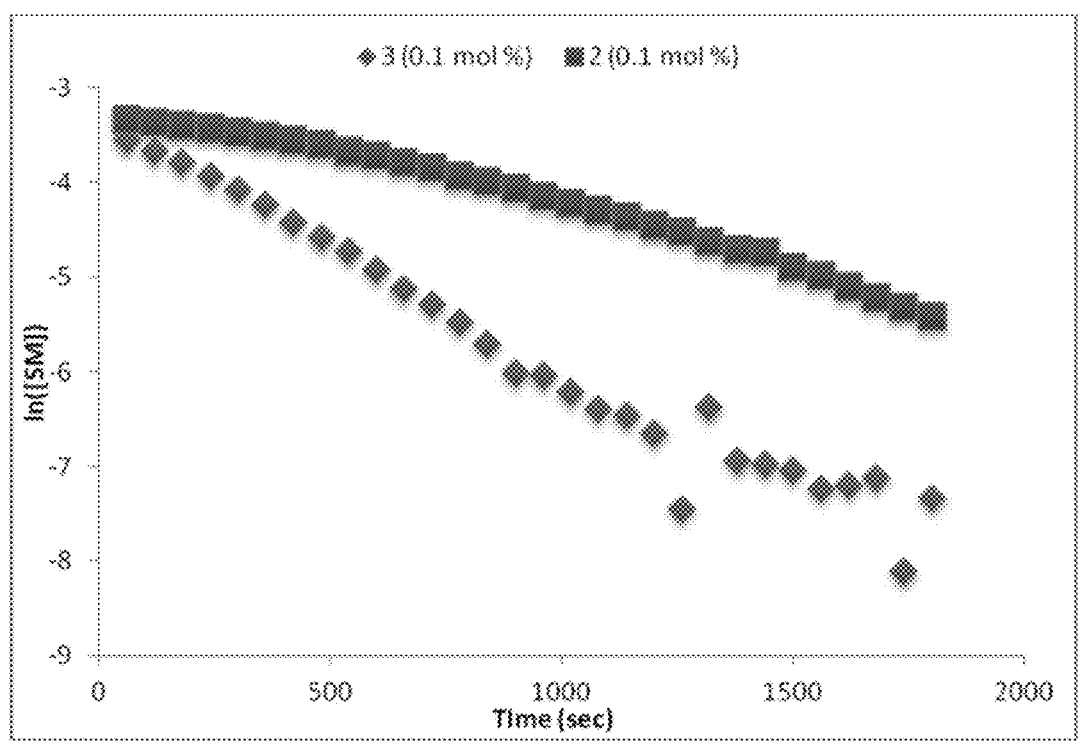
FIG. 8 summarizes the Log plots for catalyst C848 (2) and catalyst (3)-rac in the ROMP of cyclooctene of Example 3b as shown in Scheme 9.

A similar increase in selectivity was observed for the reaction described in Scheme 9. At 25% conversion, C848 (2) produced the ROMP product (14) with an (E/Z) ratio of 4:1. At that same conversion, catalyst (3)-rac gave an (E/Z) ratio of 7:1. Empirical data indicate that the thermodynamic ratio for this reaction is an (E/Z) ratio of 4:1. FIG. 7 summarizes the conversion in ROMP of cyclooctene using C848 (2) and catalyst (3)-rac. FIG. 8 summarizes the Log plots for catalyst C848 (2) and catalyst (3)-rac in the ROMP of cyclooctene.

Catalyst (3)-rac gives us insight into other promising ligand scaffolds that could be synthesized to improve both catalyst selectivity and activity for ROCM and basic CM reactions. Tuning the structure of these catalysts such that steric impedances allow for the formation of the desired stereochemistry may allow us to achieve this goal. Modification of the robust and easily tuned NHC ligand will be the key to controlling stereoselectivity. For example, by connecting the substituents on the ortho positions of each aryl group to make a tether in the NHC ligands may improve the selectivity. It is also hoped that the use of a bulky thiol ligand in place of one of the chlorides may result in pushing the two ortho groups to the same side and would also provide a steric block for the C3 position on the metallacycle to fit the model shown above.

Example 4

Cross Metathesis Reactions

Example 4a

Cross Metathesis of 5-decene with di-benzoate Substrates

Scheme 10: Cross metathesis of 5-decene with (18) DBB

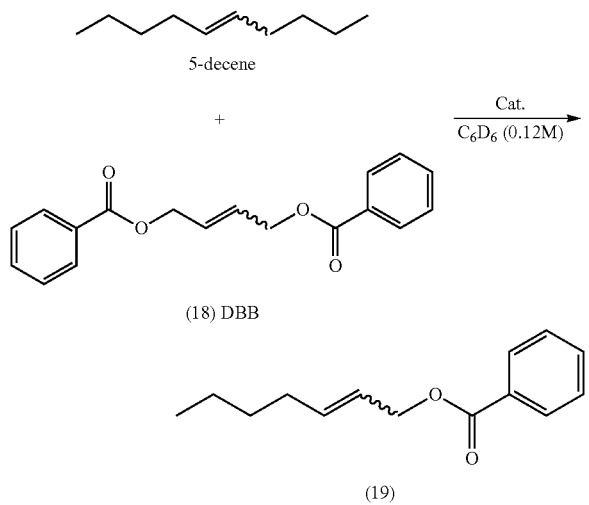

Figure 11:
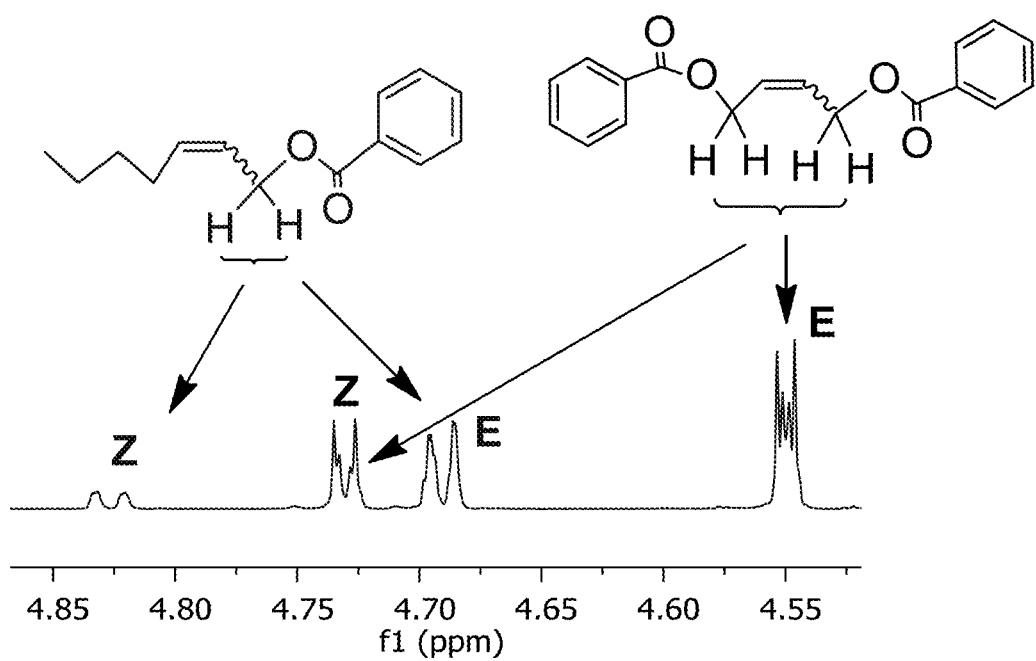
FIG. 11 shows the $^1$H NMR peaks of the allylic protons of substrate (18) and of product (19) as shown in Example 4a, reaction of Scheme 10.
Figure 12:
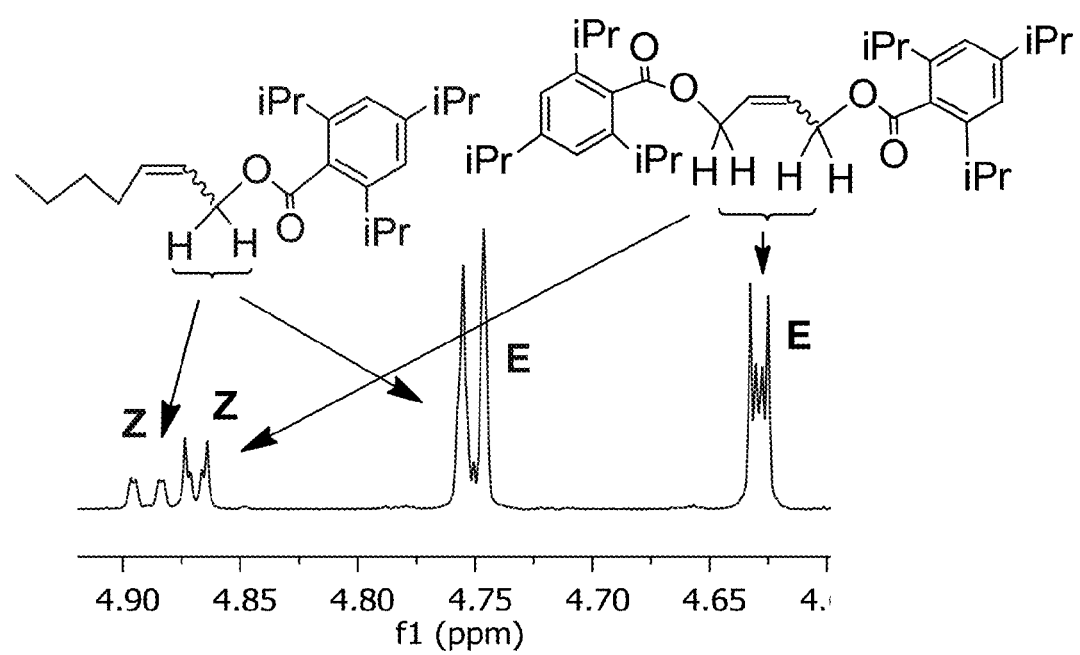
FIG. 12 shows the $^1$H NMR peaks of the allylic protons of substrate (20) and of product (21) as shown in Example 4a, reaction of Scheme 11.

The cross metathesis reaction (Scheme 10) of 5-decene with (18) DBB and cross metathesis reaction (Scheme 11) of 5-decene with (20) BTBB using ruthenium catalysts, have been monitored by $^1$H NMR. As shown in FIGS. 11 and 12, the $^1$H peaks on the allylic position of the (E) and (Z) forms are well distinguished from each other in the (18) and (20) substrates, as well as in the and the corresponding products (19) and (21). Hence, $^1$H NMR array experiments can illustrate the change of (E/Z) selectivity over the duration of the reaction.

5-Decene and (18) DBB were dissolved in dry $C_6D_6$ to give a 0.12 M solution with a 3:1 ratio of 5-decene to (18) DBB. 0.0066 M of ruthenium catalyst solution in dry $C_6D_6$ was prepared in a separate vial. In a dry NMR tube containing 0.55 mL of the above substrate solution was added an adequate amount of ruthenium catalyst solution right before starting the $^1$H NMR study. $^1$H NMR experiments were ran for 4 h at room temperature, performing a $^1$H NMR spectra every 10 minutes (600 MHz, Varian NMR, set with 45° pulse angle and 2 second relaxation delay).

Figure 13:
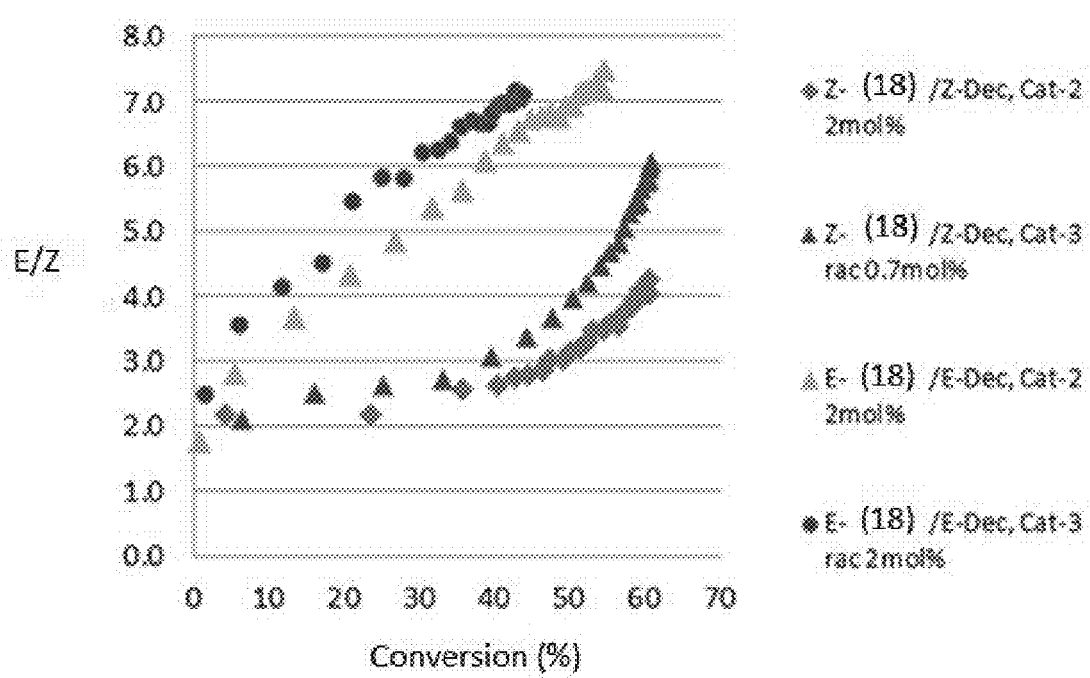
FIG. 13 shows the (E/Z) ratio of product (19) versus the conversion (%) in the cross metathesis of 5-decene with (18), as shown in Example 4a, reaction of Scheme 10.
Figure 14:
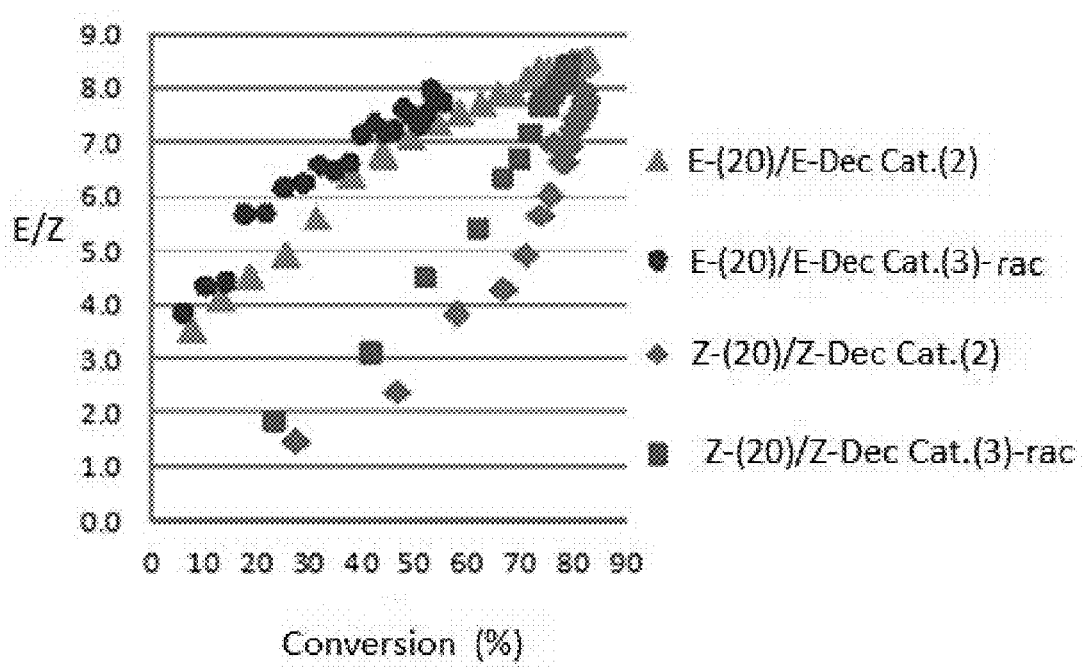
FIG. 14 shows the (E/Z) ratio of product (21) versus the conversion (%) in the cross metathesis of 5-decene with (20), as shown in Example 4a, reaction of Scheme 11.

The results of the $^1$H NMR study were summarized in Tables 2, 3, and 4 and FIGS. 13 and 14. As shown in the results, catalyst (3)-rac provided the cross metathesis product with slightly higher (E/Z) ratio than catalyst (2) in all of reactions studied. In addition, the (E) forms of (18) DBB and (20) BTBB gave a higher (E/Z) ratio of the products (19) and (21) respectively compared to the same reactions with the (Z) forms.

TABLE 2

(E/Z) Ratio of product (19) in the cross metathesis reaction of (Z)-5-decene with (Z)-(18) DBB

| Entry | Catalyst | Mol % | % Conv. (4 h) | (E/Z) ratio of (19) at 60% conversion |
|---|---|---|---|---|
| 1 | C848 (2) | 2 | 60 | 4.1 |
| 2 | C848 (2) | 5 | 67 | 4.2 |
| 3 | (3)-rac | 2 | 90 | ~6 |
| 4 | (3)-rac | 1 | 74 | 5.8 |
| 5 | (3)-rac | 0.7 | 61 | 5.8 |
| 6 | (3)-meso | 2 | 54 | 4.9* |
| 7 | C849 | 2 | 70 | 4.4 |

* at 54% conversion

TABLE 3

(E/Z) Ratio of product (19) in the cross metathesis reaction of 5-decene with (18) DBB

| Entry | Cat. 2% Mol | 5-Decene | (18) DBB | Conv. (4 h) | (E/Z) ratio of (19) at 40% conversion |
|---|---|---|---|---|---|
| 1 | C848 (2) | (Z) | (E) | 48 | 6.2 |
| 2 | C848 (2) | (E) | (E) | 54 | 6.3 |
| 3 | C848 (2) | (E) | (Z) | 63 | 2.7 |
| 4 | (3)-rac | (Z) | (E) | 42 | 6.8 |
| 5 | (3)-rac | (E) | (E) | 44 | 6.9 |
| 6 | (3)-rac | (E) | (Z) | 77 | ~4 |
| 7 | (3)-meso | (E) | (E) | 40 | 6.9 |

Scheme 11: Cross metathesis of 5-decene with (20) BTBB

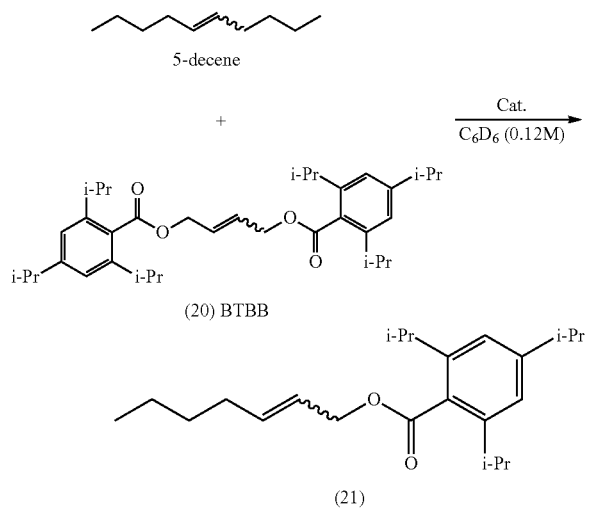

TABLE 4

(E/Z) Ratio of product (21) in the cross metathesis reaction of 5-decene with (20) BTBB

| Entry | Cat. 2% Mol | 5-Decene | (20) BTBB | Conversion (4 h) | (E/Z) ratio of (21) |
|---|---|---|---|---|---|
| 1 | C848 (2) | (Z) | (Z) | 82 | ~4* |
| 2 | (3)-rac | (Z) | (Z) | 79 | ~5* |

TABLE 4-continued (E/Z) Ratio of product (21) in the cross metathesis reaction of 5-decene with (20) BTBB

| Entry | Cat. 2% Mol | 5-Decene | (20) BTBB | Conversion (4 h) | (E/Z) ratio of (21) |
|---|---|---|---|---|---|
| 3 | C848 (2) | (E) | (E) | 83 | 7.2** |
| 4 | (3)-rac | (E) | (E) | 55 | 7.5** |

*at 60% conversion
**at 50% conversion

Extension of these catalysts to the (E)-selective olefin metathesis will enable an elegant approach to the application of natural product synthesis and pharmaceutical area.

What is claimed is:

1. A compound represented by Formula (IV):

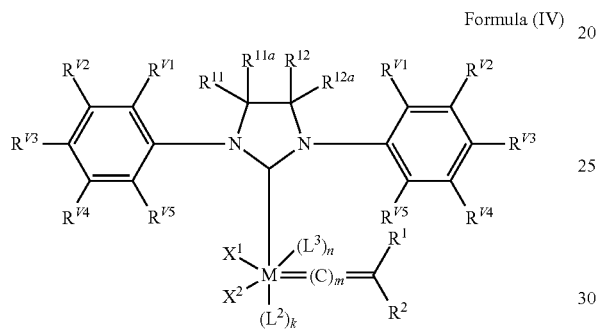

Formula (IV)

wherein:

M is a Group 8 transition metal;

$R^{V1}$, $R^{V2}$, $R^{V3}$, $R^{V4}$ and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, or substituted $C_5$-$C_{14}$ aryl;

$R^{11}$, $R^{12}$, $R^{11a}$ and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide;

$X^1$ and $X^2$ are independently halogen;

$L^2$ and $L^3$ are neutral electron donor ligands, wherein $L^2$ and/or $L^3$ may be linked with $R^1$ or $R^2$ to form one or more cyclic groups;

n is 0 or 1;

m is 0, 1, or 2;

k is 0 or 1;

$R^1$ and $R^2$ are independently selected from hydrogen, hydrocarbyl, substituted hydrocarbyl, heteroatom-containing hydrocarbyl, or substituted heteroatom-containing hydrocarbyl;

at least one of $R^{V1}$, $R^{V2}$, $R^{V3}$, $R^{V4}$ or $R^{V5}$ is represented by a group selected from:

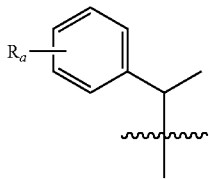

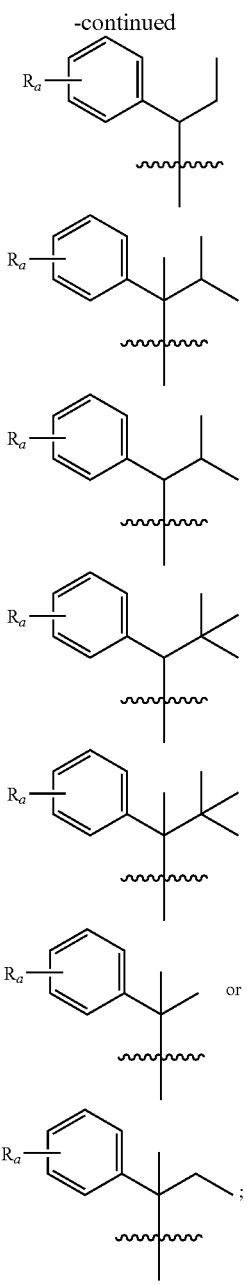

"a" represents 0, 1, 2, 3, 4 or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl or halogen.

2. The compound according to claim 1, wherein

M is Ru;

n is 0;

m is 0;

k is 1;

$X^1$ and $X^2$ are independently halogen;

$L^2$ is a neutral electron donor ligand; and $R^{11}$, $R^{12}$, $R^{11a}$ and $R^{12a}$ are independently hydrogen.

3. The compound according to claim 2, wherein:

$R^{V1}$, $R^{V2}$, $R^{V3}$, $R^{V4}$ and $R^{V5}$ are independently hydrogen or substituted branched $C_1$-$C_6$ alkyl; and at least one of $R^{V1}$, $R^{V2}$, $R^{V3}$, $R^{V4}$ or $R^{V5}$ is represented by a group selected from:

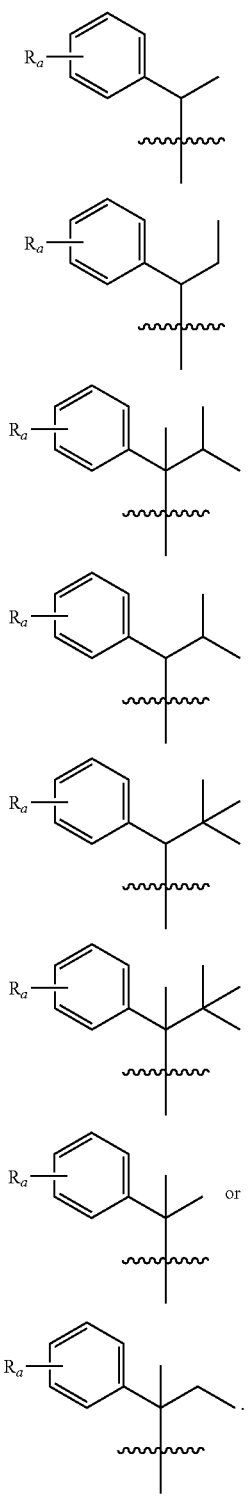

4. The compound according to claim 3, wherein:
$R^{V1}$, $R^{V2}$, $R^{V3}$ and $R^{V4}$ are independently hydrogen;
$X^1$ and $X^2$ are independently chloride;
$L^2$ is $PCy_3$;
$R^1$ is hydrogen;
$R^2$ is phenyl;

$R^{V5}$ is

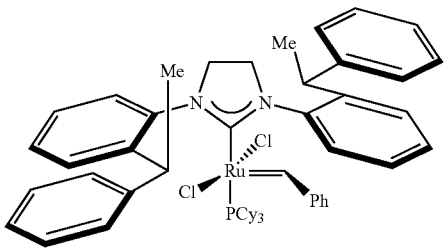

and
"a" is 0.

5. The compound according to claim 3, wherein the compound is in a racemic isomeric form, a meso isomeric form, or a mixture of the racemic and meso isomeric forms.

6. The compound according to claim 1, wherein the compound is in a racemic isomeric form, a meso isomeric form, or a mixture of the racemic and meso isomeric forms.

7. The compound according to claim 1, wherein the compound is:

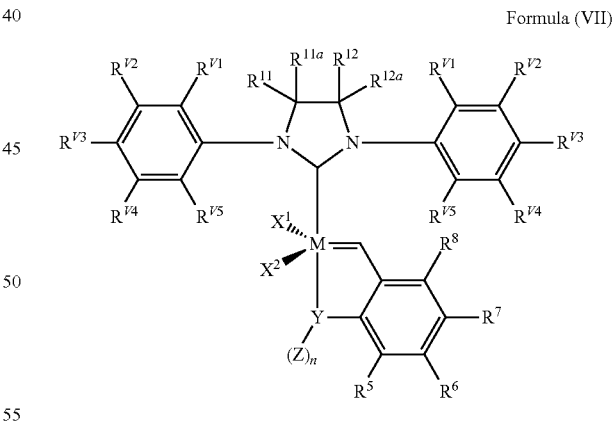

8. The compound according to claim 7, wherein the compound is in a racemic isomeric form, a meso isomeric form, or a mixture of the racemic and meso isomeric forms.

9. A compound represented by Formula (VII):

Formula (VII)

wherein:
M is Ru or Os;
$R^{V1}$, $R^{V2}$, $R^{V3}$, $R^{V4}$ and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, or substituted $C_5$-$C_{14}$ aryl;
$R^{11}$, $R^{12}$, $R^{11a}$ and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide;

$X^1$ and $X^2$ are independently halogen;

Y is a heteroatom selected from N, O, S, or P;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, and borate;

n is 0, 1, or 2;

Z is a group selected from hydrogen, alkyl, aryl, functionalized alkyl, functionalized aryl; and at least one of $R^{V1}$, $R^{V2}$, $R^{V3}$, $R^{V4}$ or $R^{V5}$ is represented by a group selected from:

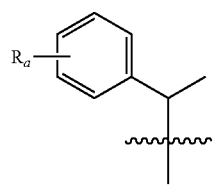

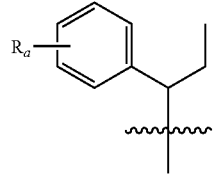

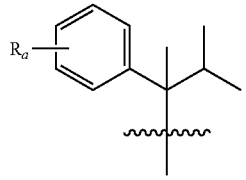

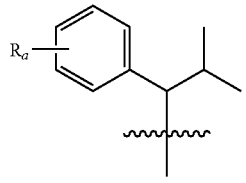

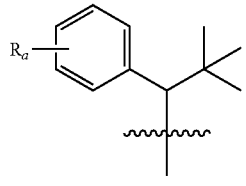

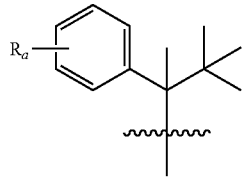

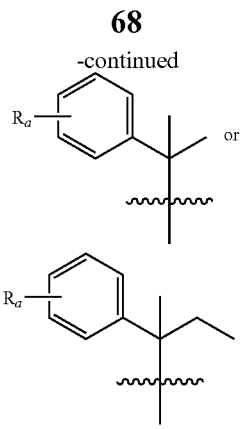

"a" represents 0, 1, 2, 3, 4 or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl or halogen.

10. The compound according to claim 5 wherein:

M is Ru;

$X^1$ and $X^2$ are each chloride;

Y is O;

$R^5$, $R^6$, $R^7$, and $R^8$ are each hydrogen;

n is 1;

Z is iso-propyl;

$R^{V1}$, $R^{V2}$, $R^{V3}$ and $R^{V4}$ are independently hydrogen;

$R^{11}$, $R^{12}$, $R^{11a}$ and $R^{12a}$ are independently hydrogen;

$R^{V5}$ is

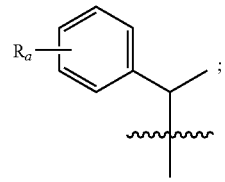

and

"a" represents 0.

11. The compound according to claim 9, wherein the compound is:

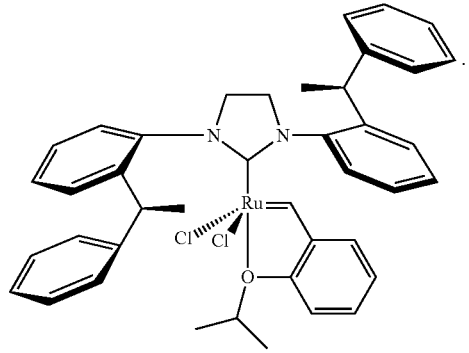

12. The compound of according to claim 11, wherein the compound is in a racemic isomeric form, a meso isomeric form, or a mixture of the racemic and meso isomeric forms.

13. A method for performing a metathesis reaction comprising, contacting at least one olefin with a compound of Formula (IV) or Formula (VII), wherein:

the compound of Formula (IV) is represented by

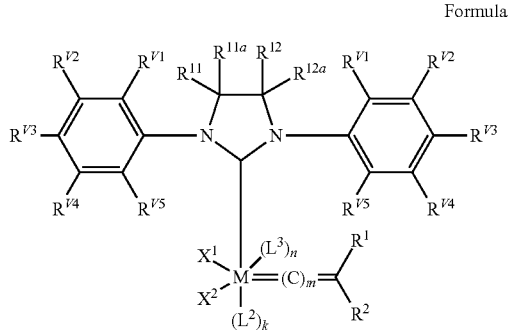

Formula (IV)

wherein:

M is a Group 8 transition metal;

$R^{V1}$, $R^{V2}$, $R^{V3}$, $R^{V4}$ and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, or substituted $C_5$-$C_{14}$ aryl;

$R^{11}$, $R^{12}$, $R^{11a}$ and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide, $X^1$ and $X^2$ are independently halogen;

$L^2$ and $L^3$ are neutral electron donor ligands, wherein $L^2$ and/or $L^3$ may be linked with $R^1$ or $R^2$ to form one or more cyclic groups;

n is 0 or 1;

m is 0, 1, or 2;

k is 0 or 1;

$R^1$ and $R^2$ are independently selected from hydrogen, hydrocarbyl, substituted hydrocarbyl, heteroatom-containing hydrocarbyl, or substituted heteroatom-containing hydrocarbyl;

at least one of $R^{V1}$, $R^{V2}$, $R^{V3}$, $R^{V4}$ or $R^{V5}$ is represented by a group selected from:

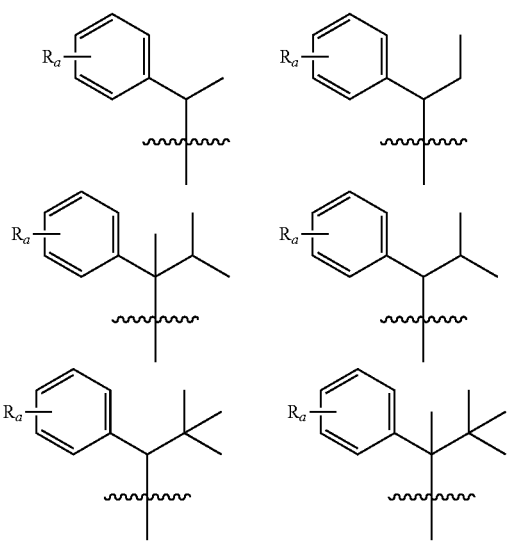

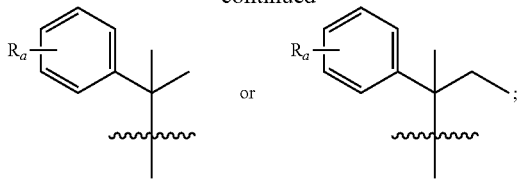

"a" represents 0, 1, 2, 3, 4 or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl or halogen; and the compound of Formula (VII) is represented by

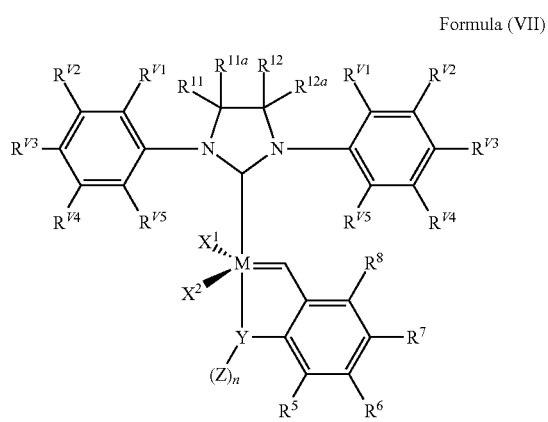

Formula (VII)

wherein:

M is Ru or Os;

$R^{V1}$, $R^{V2}$, $R^{V3}$, $R^{V4}$ and $R^{V5}$ are independently hydrogen, substituted branched $C_1$-$C_6$ alkyl, $C_4$-$C_{10}$ cycloalkyl, substituted $C_4$-$C_{10}$ cycloalkyl, $C_4$-$C_{10}$ heteroatom-containing cycloalkyl, substituted $C_4$-$C_{10}$ heteroatom-containing cycloalkyl, $C_5$-$C_{14}$ aryl, or substituted $C_5$-$C_{14}$ aryl;

$R^{11}$, $R^{12}$, $R^{11a}$ and $R^{12a}$ are independently hydrogen, $C_1$-$C_{12}$ alkyl, substituted $C_1$-$C_{12}$ alkyl, $C_1$-$C_{12}$ alkoxy, substituted $C_1$-$C_{12}$ alkoxy, $C_5$-$C_{14}$ aryl, substituted $C_5$-$C_{14}$ aryl, or halide;

$X^1$ and $X^2$ are independently halogen;

Y is a heteroatom selected from N, O, S, or P;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, and borate;

n is 0, 1, or 2;

Z is a group selected from hydrogen, alkyl, aryl, functionalized alkyl, functionalized aryl; and at least one of $R^{V1}$, $R^{V2}$, $R^{V3}$, $R^{V4}$ or $R^{V5}$ is represented by a group selected from:

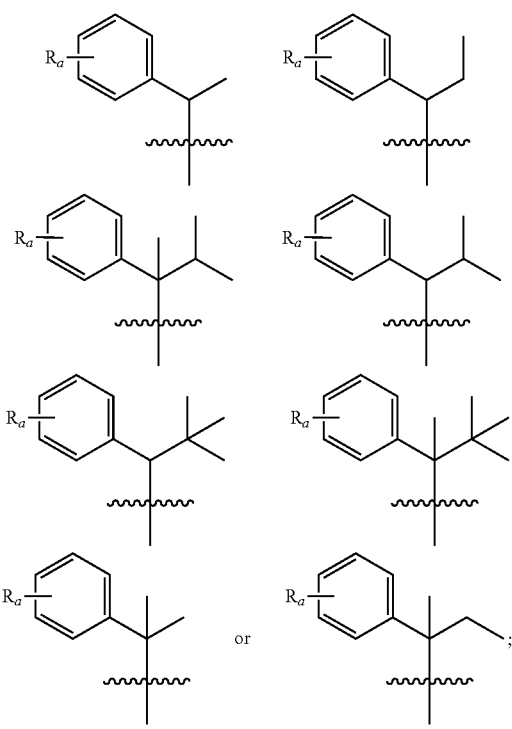

or

"a" represents 0, 1, 2, 3, 4 or 5; and

R is substituted $C_1$-$C_6$ alkyl, $C_1$-$C_6$ alkyl, substituted $C_3$-$C_{10}$ cycloalkyl, $C_3$-$C_{10}$ cycloalkyl or halogen.

14. The method according to claim 13, wherein the metathesis reaction is a ring closing metathesis reaction.

15. The method according to claim 13, wherein the metathesis reaction is a ring opening cross metathesis reaction.

16. The method according to claim 13, wherein the metathesis reaction is a cross metathesis reaction.

17. The method according to claim 16, wherein the cross metathesis reaction comprises at least one internal olefin reactant.

18. The method according to claim 13, wherein the metathesis reaction is a ring opening metathesis polymerization reaction.

19. The method according to claim 18, wherein the ring opening metathesis polymerization reaction comprises at least one cyclic olefin reactant.

20. The method according to claim 13, wherein the compound of Formula (IV) or Formula (VII) may be is in a racemic isomeric form, a meso isomeric form, or a mixture of the racemic and meso isomeric forms.

21. The method according to claim 13, wherein the compound of Formula (IV) is:

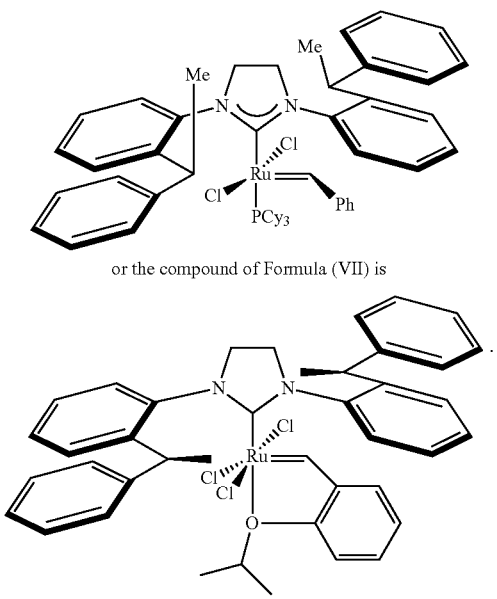

or the compound of Formula (VII) is

22. The method according to claim 21, wherein the compound of Formula (IV) or Formula (VII) is in a racemic isomeric form, a meso isomeric form, or a mixture of the racemic and meso isomeric forms.

* * * * *